(12) United States Patent
Costella et al.

(10) Patent No.: US 12,336,822 B2
(45) Date of Patent: Jun. 24, 2025

(54) METHODS OF MAKING FLEXIBLE ELECTRODES

(71) Applicant: LUNA INNOVATIONS INCORPORATED, Roanoke, VA (US)

(72) Inventors: Lauren Anne Costella, Roanoke, VA (US); Christopher K. Tison, Roanoke, VA (US); Melissa Skoff, Roanoke, VA (US); David Remer, Roanoke, VA (US); Kelsey Broderick, Roanoke, VA (US)

(73) Assignee: LUNA LABS USA, LLC, Charlottesville, VA (US)

( * ) Notice: Subject to any disclaimer, the term of this patent is extended or adjusted under 35 U.S.C. 154(b) by 751 days.

(21) Appl. No.: 17/435,850

(22) PCT Filed: Mar. 6, 2020

(86) PCT No.: PCT/US2020/021305
§ 371 (c)(1),
(2) Date: Sep. 2, 2021

(87) PCT Pub. No.: WO2020/181155
PCT Pub. Date: Sep. 10, 2020

(65) Prior Publication Data
US 2022/0151530 A1    May 19, 2022

Related U.S. Application Data

(60) Provisional application No. 62/814,385, filed on Mar. 6, 2019.

(51) Int. Cl.
*A61B 5/263* (2021.01)
*A61N 1/05* (2006.01)
(Continued)

(52) U.S. Cl.
CPC ............ *A61B 5/263* (2021.01); *A61N 1/0551* (2013.01); *D01D 5/0076* (2013.01);
(Continued)

(58) Field of Classification Search
CPC ..... A61B 5/263; A61B 5/27; A61B 2562/125; Y10T 29/49117
(Continued)

(56) References Cited

U.S. PATENT DOCUMENTS 7,326,649 B2 * 2/2008 Rodger ................ A61N 1/0551
257/737
9,847,211 B2 * 12/2017 Zhu .......................... G06F 3/045
2006/0003090 A1 1/2006 Rodger et al.

FOREIGN PATENT DOCUMENTS

WO    WO 2015/153907    10/2015

OTHER PUBLICATIONS

Communication pursuant to Article 94(3) EPC, EP Application No. 20716285.0, Apr. 3, 2024.
(Continued)

*Primary Examiner* — Thiem D Phan
(74) *Attorney, Agent, or Firm* — Nixon & Vanderhye P.C.

(57) ABSTRACT

The novel flexible electrodes disclosed herein utilize the low bending stiffness of electrospun nanofiber mats to achieve the material properties required for surgical implantation and sustained bidirectional communication with peripheral nerves without compromising electronic functionality. According to certain embodiments disclosed herein, implantable neural electrode probes are provided which comprise a polymeric substrate having proximal and distal ends, an electrode interface at the proximal end of the substrate; at least one neural contact at the distal end of the substrate; and electrically conductive traces formed on the fibrous substrate providing electrical communication
(Continued)

between the at least one neural contact and the electrode interface, wherein the substrate comprises a nonwoven mass of polymeric nanofibers.

20 Claims, 26 Drawing Sheets

(51) Int. Cl.
*D01D 5/00* (2006.01)
*D04H 1/4334* (2012.01)
*D04H 1/728* (2012.01)
*D06M 11/83* (2006.01)
*D06M 15/233* (2006.01)
*D06M 15/356* (2006.01)
*D06M 101/34* (2006.01)

(52) U.S. Cl.
CPC ........... *D04H 1/4334* (2013.01); *D04H 1/728* (2013.01); *D06M 11/83* (2013.01); *D06M 15/233* (2013.01); *D06M 15/3568* (2013.01); *A61B 2562/125* (2013.01); *D06M 2101/34* (2013.01); *D10B 2403/02431* (2013.01); *D10B 2509/00* (2013.01); *Y10T 29/49117* (2015.01)

(58) Field of Classification Search
USPC .................................. 29/825, 428, 846, 876
See application file for complete search history.

(56) References Cited

OTHER PUBLICATIONS

International Search Report for PCT/US2020/021305, mailed Jun. 19, 2020, 5 pages.
Written Opinion of the ISA for PCT/US2020/021305, mailed Jun. 19, 2020, 10 pages.
Dong Nyoung Heo et al., "Flexible and Highly Biocompatible Nanofiber-Based Electrodes for Neural Surface Interfacing", ACS Nano, vol. 11, No. 3, Feb. 17, 2017, pp. 2961-2971.
Boretius et al., "A transverse intrafascicular multichannel electrode (TIME) to interface with the peripheral nerve", Biosensors and Bioelectronics, vol. 26, No. 1, Sep. 15, 2010, pp. 62-69.
Tingrui Pan et al., "From Cleanroom to Desktop: Emerging Micro-Nanorabrication Technology for Biomedial Applications", Annals of Biomedical Engineering, vol. 39, No. 2, Dec. 14, 2010, pp. 600-620.
Číková et al., "Conducting electrospun polycaprolactone/polypyrrole", Synthetic Metals, vol. 235, Dec. 11, 2017, pp. 80-88.
Harris et al., "In vivo deployment of mechanically adaptive nanocomposites for intracortical microelectrodes; In vivo deployment of mechanically adaptive nanocomposites for intracortical microelectrodes", Journal of Neural Engineering, vol. 8, No. 4, Jun. 8, 2011, p. 46010.
Zhang et al., "Preparation of porous nylon 6 fiber via electrospinning", Polymer Engineering & Science, vol. 55, No. 5, Jul. 18, 2014, pp. 1133-1141.

* cited by examiner

Insulating: Nylon-6 nanofibers
Conducting: 10% PVA with 1% SP electrosprayed particles Insulating: Nylon-6 nanofibers
Conducting: 12% PCL + 0.06% SP and 10% PVA + 1% SP nanofibers

METHODS OF MAKING FLEXIBLE ELECTRODES

CROSS-REFERENCE TO RELATED APPLICATION

This application is the U.S. national phase of International Application No. PCT/US2020/021305 filed Mar. 6, 2020, and is based on and claims priority benefits from U.S. Provisional Application Ser. No. 62/814,385 filed on Mar. 6, 2019, the entire contents of each of which are expressly incorporated hereinto by reference.

GOVERNMENT RIGHTS

This invention was made with Government support under the following Government awarded contracts: DARPA D16PC00095 and DARPA D17PC00125. The Government has certain rights to the invention.

FIELD

The disclosed embodiments herein relate generally to advanced nano-fiber based materials systems that are employed in electronic applications. According to certain embodiments, the nano-fiber based materials systems are especially usefully employed as electrodes in a variety of applications, such as biomedical applications, due to their enhanced flexibility which closely matches surrounding tissue in or on which the electrodes are employed.

BACKGROUND

Flexible electrodes can find application in diverse fields such as bioengineering (implantable sensors, spinal implants, neural interfaces), wearable sensors, heating elements, and more. The ability to provide patterned electrodes is critical for these functions, but maintaining flexibility is particularly difficult. The use of flexible electronic interfaces for neural interfacing is used as the primary example throughout. By way of example, breakthroughs in the development of neural interface technologies have been prevalent over the last decade. These advancements have included state-of-the-art prosthetics controlled by neural interfacing electrodes as well as implementation of sensitization using these interfaced prosthetics. Together, these advances have the potential to improve the quality of life for amputees by replacing lost limbs with advanced prosthetics. However, as the potential of these technologies continues to advance, their clinical application is limited by the current lack of long-term stability and precision of the electrodes.

The two primary limiting complications with existing neural interface technologies are tissue damage and mechanical failure of the device over time. Even state-of-the-art technologies, such as the transverse intrafascicular multichannel electrode (TIME) and Utah slanted electrode array (USEA), exert high mechanical strain on surrounding tissue during insertion, resulting in scarring, bleeding, and nerve tissue damage. This is largely due to significant mismatches in mechanical properties between the implanted electrode and the tissue into which it is being implanted. For example, tissue in the peripheral nervous system (PNS) has an elastic modulus in the 0.5-1.0 MPa range, while platinum and silicon (standard electrode interface materials) have elastic moduli of 168,000 and 180,000 MPa, respectively. This 5-6 order of magnitude discrepancy in elastic modulus and other mechanical properties leads to a variety of implantation and chronic use issues such as tissue damage, difficult surgical attachment, and relative motion during use. Most critically for performance, it also leads to the phenomena of glial scarring (or encapsulation) whereby mechanical damage, cell death, and inflammatory response result in glial cell encapsulation of the interface. This prohibits electrical contact with nerves, eliminating interface function. Addressing the need for nerve interfacing technologies that can be placed and used chronically with a reduction in complications will require electrode materials with mechanical properties more closely matched to native tissue. However, these materials must simultaneously possess the mechanical properties needed for nerve penetration and placement as well as the electrical conductivity and interface arrangement for use with existing electrophysiology equipment.

The problem common to neural interfacing designs and other devices where electrode flexibility is required is the material constraints that exist on each system. The peripheral nerve can sustain up to 10% strain during the course of normal human movement, which is a level of deformation that many of the currently utilized electrodes cannot undergo without exerting significant stresses on the surrounding delicate neural tissue. The material property mismatch between the nerve and implant often leads to encapsulation and scarring between the electrode and nerve fibers, which significantly decreases the signal-to-noise ratio and the resultant sensitivity of the electrode. The application of biological or softening materials provides better matching to native tissue properties, but electrodes still typically contain wire conducting elements that are not softening and retain material mismatch issues. Removable or dissolvable carrier systems often leave void space that fills in with scar tissue, or may degrade into byproducts that result in swelling, nerve impingement, inflammation, and electrode encapsulation. Biocompatible polymers such as polyimide, silicone, or PTFE have shown great promise for softer insulating layers, but the materials used for the conductive contact (e.g. platinum, iridium, or gold) typically have stiffness values that are orders of magnitude larger than that of neural tissue (600 kPa) Similar bending concerns exist for wearable sensors that may be integrated into textiles or work on the skin, where bending strains of greater than 10% are routinely expected.

The inability to properly match the material properties of neural interfacing devices to native tissues has limited the implementation of newly developed neural interfacing technologies. It would therefore be highly desirable if neural interfacing devices could be provided which more properly match the physical attributes of native tissue. Similarly, flexible electrode material systems would also enable use in wearable sensors and related devices. It is towards providing such solutions that the embodiments disclosed herein are directed.

SUMMARY

In order to address the five to six order of magnitude discrepancy in elastic modulus in relation to native tissue that currently exists, the embodiments disclosed herein provide a unique nanofiber-based material interface system. The novel materials systems disclosed herein utilize the low bending stiffness of electrospun nanofiber mats to achieve the material properties required for surgical implantation and sustained bidirectional communication with human tissue, specifically peripheral nerves, without compromising electronic functionality. According to certain embodiments, the novel material technology disclosed herein is especially useful when embodied as a transverse intrafascicular multichannel electrode (TIME) system, but may also be applicable to other future neural interface technologies. It is also likely that similar systems, in which the unique electrically-patterned nanofiber substrate provides soft tissue-like mechanical properties, could also be used for other surgically implanted products or wearable sensors and heating elements.

The unique aspects of the embodiments disclosed herein include:

A nanofiber-based insulating and support layer providing high sample flexibility while maintaining sufficient strength to allow the device to be easily implanted and surgically tethered.

A nanofibrous metal-based or polymer-based conductive layer reduces modulus mismatch and provides stable mechanical, electrical, and chemical properties during chronic implantations.

Materials-based electrode design is not "device specific" and therefore serves as an enabling platform for multiple neural interfaces and flexible electronic applications.

As noted above, the neural-interfacing materials system of the disclosed embodiments is especially useful for application with the TIME nerve interface design, but the disclosed embodiments may have application in multiple neural interfacing and biological applications. The novel materials system as disclosed herein that is inherently flexible, but possesses the tensile strength required for handling and insertion in vivo could for example find other potential applications in cranial electrode implants, muscle/musculoskeletal electrodes, and wearable surface electrodes. The flexibility of the novel materials system as disclosed herein may therefore be capable of providing bi-directional communication between in vivo neural and external electronic devices.

According to certain embodiments disclosed herein, flexible electrodes are provided which comprise a fibrous substrate which includes a mass of polymeric nanofibers, and electrically conductive traces formed on the fibrous substrate providing electrical communications between at least one contact of the electrode and an electrode interface. The fibrous substrate may exhibit a flexibility of about 50 MPa to about 5 GPA and be formed of polymeric nanofibers may be formed of a plastic material selected from the group consisting of nylon, polycaprolactone, cellulose acetate, poly(methyl-methacrylate, ethylene vinyl alcohol and polyimide. Preferred are nylon-6 and nylon-6,12 nanofibers.

A stabilizing cuff may be attached to a proximal portion of the fibrous substrate. In order to further enhance stability, a support fiber formed of a high strength polymer, e.g., ultra high density polyethylene or polyaramid, may be attached axially to the substrate.

According to certain embodiments, the substrate may comprise a nanofiber layer which includes the polymeric nanofibers and an insulation layer, e.g., p-xylyene polymer or p;olydimethylsiloxane.

The fibrous substrate may comprise an electrically conductive polymer component, e.g., poly(3,4-ethylenedioxythiophene) polystyrene sulfate and vapor phase polymerized poly(3,4-ethylenedioxythiophene) metallic coating (e.g., gold) deposited on the nanofiber substrate and/or nanofibers formed of polycaprolactone, cellulose acetate, poly(methyl-methacrylate) and ethylene vinyl alcohol. The polymeric nanofibers may comprise an insulating coating, e.g., p-xylyene polymer or polydimethylsiloxane.

The flexible electrodes disclosed herein may be formed by electrospinning a substrate layer comprised of a nonwoven mass of polymeric nanofibers, depositing a conductive component on or within the nanofiber substrate, followed by photolithographically forming electrical traces in the substrate layer. The substrate layer may be coated with a silicone layer, and thereafter regions may be etched into the silicone layer to form contact points. The final shape of the electrode may then be formed by removing excess material.

These and other aspects of the present invention will become more clear after careful consideration is given to the following detailed description of a presently preferred exemplary embodiment thereof.

BRIEF DESCRIPTION OF THE DRAWINGS

Reference will be made to the accompanying drawing Figures, wherein:

FIG. 7A depicts the ultimate tensile strength (UTS), FIG. 7B depicts the percent (%) elongation, FIG. 7C depicts the elastic modulus (MPa) and FIG. 7D depicts the toughness (MPa);

FIGS. 8A-8D are bar graphs depicting results of property testing for Nylon-6 and Parylene-C coated Nylon-6 for samples that were tested dry and hydrated, respectively, wherein the symbol * indicates significance at $\alpha=0.05$, and wherein FIG. 8A depicts the ultimate tensile strength (UTS), FIG. 8B depicts the percent (%) elongation, FIG. 8C depicts the elastic modulus (MPa) and FIG. 8D depicts the toughness (MPa);

FIG. 18A shows the nylon-6 strips on the wafer, FIG. 18B shows the strips after removal from the substrate and FIG. 18C is a SEM image of a 50 μm patterned nylon-6 features;

DETAILED DESCRIPTION

The embodiments disclosed herein are based on the novel application of electrospun nanofibers as a flexible substrate for patterning conductive traces. Such embodiments therefore enable better mechanical matching of biological tissue properties, specifically neural tissue in this indication, while maintaining the electrical properties required for bidirectional communication with advanced prosthetics or other machine interfaces. This novel materials approach as disclosed herein capitalizes on the inherent flexibility and biocompatibility of nanofiber mats and demonstrates the potential of utilizing these substrates with advanced lithography patterning methods to create ultraflexible materials for biomedical applications.

Figure 1:
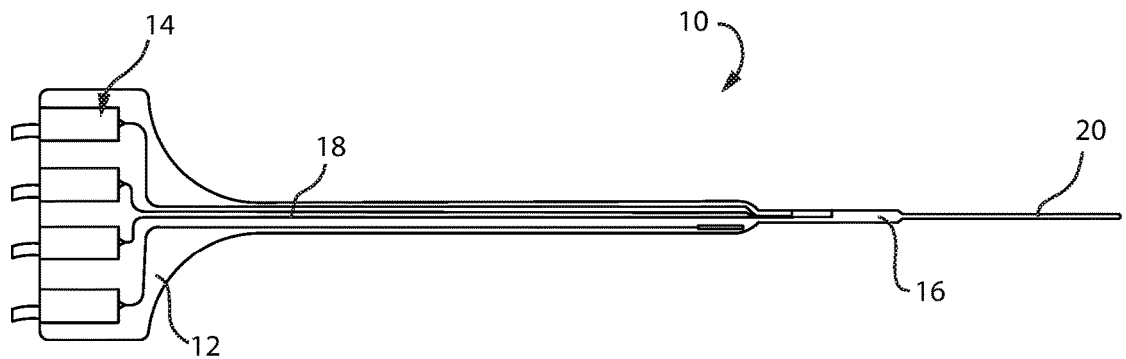
FIG. 1 is a plan view illustrating a neural interface device in accordance with an embodiment of this invention.

An implantable neural electrode 10 in accordance with an embodiment of this invention is depicted in FIG. 1. As shown, the electrode 10 includes a substrate 12 formed of a non-woven mass of electrospun nanofibers having an electrical interface 14 (e.g., a TIME interface) at a proximal end thereof and one or more contacts 16 (e.g., SIROF-coated contacts) at a distal end thereof. Conductive traces 18 (e.g., gold or PEDOT conductive layers) electrically connect the contacts 16 with the electrical interface 14. The nanofiber substrate 12 may extend beyond the contacts 16 so as to form an axially aligned insertion tip 20.

The nanofibers forming the substrate 12 are preferably of indefinite length having an average diameter of no more than about 100 nm to about 750 nm, typically between about 300 nm to about 500 nm.

The nanofibers forming the substrate 12 may be formed of any suitable polymeric material that is biologically compatible for insertion into mammalian tissue yet sufficiently flexible to achieve the desired flexibility characteristics. Specific preferred polymeric materials that may be electrospun to form the substrate 12 include, for example, nylon homopolymers and copolymers, nylon-6 and nylon 6/12, polycaprolactone and polyimide.

The substrate 12 should also exhibit sufficient flexibility to facilitate implantation and/or wearability. Specifically, it is preferred that the substrate exhibit an elastic modulus of less than about 160 GPA, typically between about 50 MPa and about 5 GPa.

The embodiments of the invention will be further described in greater detail below.

Components

A. Insulating Nanofibers

The devices disclosed herein include a nanofiber-based interface for bidirectional communication with the peripheral nervous system based on the TIME interface. Since device stiffness scales cubically with the characteristic dimension of the system, the use of nanofibers means that even with a high linear tensile strength, the bending stiffness of the nanoscale fibers will be exceptionally low. Therefore, it is possible according to the disclosed embodiments to utilize electrospun nanofibers to maximize the device flexibility and minimize the mechanical stress exerted on surrounding neural tissue following implantation. Simultaneously, the linear tensile strength of the material required for insertion and long-term stability of the device can be maintained.

One exemplary embodiment of nanofibers that may usefully be employed as an insulating template for the devices embodying the present invention are electrospun polyamide-6 (Nylon-6) nanofibers. Such electrospun Nylon-6 nanofibers are advantageous due to the compatibility of the Nylon-6 polymer with in vivo applications and its high linear tensile strength in nanofiber form. Both standard needle-based and scaled-up needle-free (Elmarco NanoSpider®) electrospinning methods of producing non-woven mats of the Nylon-6 nanofibers may be satisfactorily employed. Other polymeric nanofibers, in addition to Nylon-6, may include, for example, nanofibers electrospun from polycaprolactone, Nylon-6/12 and polyimide.

B. Conductive Polymer Layer

The implantable devices as disclosed herein may also include a nanofiber-based conductive layer for similar reasons as those mentioned hereinabove. Suitable conductive layers may be formed from nanofibers electrospun from poly(vinyl alcohol), chitosan, cellulose acetate, poly(L-lactic acid), poly(D,L-lactic acid), poly(methyl-methacrylate), and polycaprolactone that may be doped with various conductive carbon fillers (e.g., graphene, graphene oxide, carbon nanotubes and carbon nanoparticles), as well as core-sheath electrospun nanofibers in which a carbon-doped sheath polymer may be pulled into a nanofiber structure using a less-doped core nanofiber material.

Oxidative polymerization of the conductive polymer poly (3,4-ethylenedioxythiophene) (PEDOT) onto a nanofiber template by incorporating the monomer, 3,4-ethylenedioxythiophene (EDOT), into various polymeric nanofiber chemistries (polycaprolactone, cellulose acetate, poly(methyl-methacrylate), ethylene vinyl alcohol) and exposing the resultant electrospun mats to oxidant solutions (iron chloride, ammonium persulfate) may also be employed. If used, the bulk conductivity values required for neural interfacing applications should be greater than about 100 S/cm). Table 1 below show various components and end-use applications for the materials described herein.

Figure 2A:
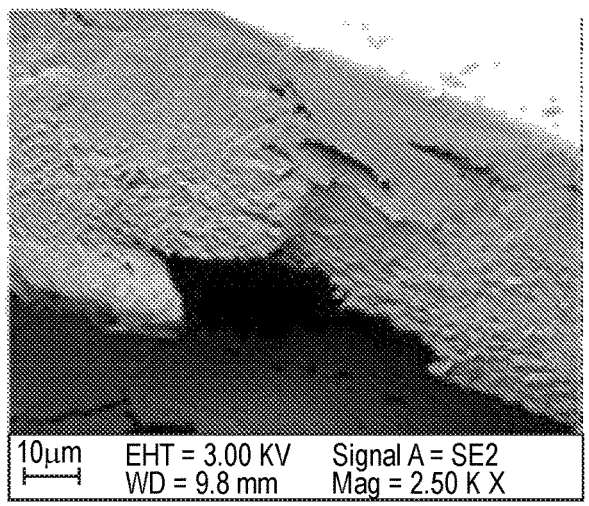
FIGS. 2A and 2B are photomicrographs of poly(3,4-ethylenedioxythiophene) polystyrene sulfate (PEDOT: PSS) material and vapor phase polymerized poly(3,4-ethylenedioxythiophene) (VPP PEDOT) material, respectively, that may be employed as a conductive component in the substrate for the neural interface device shown in FIG. 1.
Figure 2B:
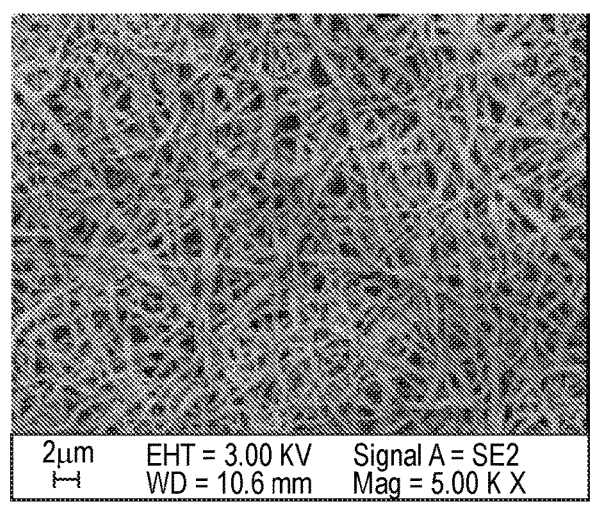

PEDOT, which forms with the anion p-toluene sulfonate (pTS) and results in a highly-flexible conductive nanofiber mat structure may also be employed. For the VPP PEDOT product, the oxidant component is electrospun within a polyvinylpyrrolidone (PVP) nanofiber structure, and subsequently exposed to EDOT vapors that initiate the polymerization reaction on the nanofiber structure. The PVP nanofiber template is subsequently dissolved in methanol, leaving a nanofibrous PEDOT structure (see FIG. 2B). Additionally, the nanofibrous morphology allows electrolyte penetration into the conductive layer, increasing charge-transfer capacity as compared to a solid PEDOT film via the increased surface area, and potentially encouraging cellular penetration and adhesion. SEM images of each formulation are shown in FIGS. 2A and 2B.

Another alternative embodiment of such vapor phase polymerization involves casting an aqueous solution of the oxidant component (iron toluene-sulfonate, iron chloride, or ammonium persulfate (APS), preferably APS) within the nanofiber structure (typically Nylon-6). This oxidant com-

TABLE 1

| Insulating Components | | | |
|---|---|---|---|
| Nylon-6 | 82 MPa | Insulating | Fibrous nature impairs electrolytic insulation |
| Parylene-C | 3460 MPa | Insulating | Nanofiber coating for improved insulation/patterning |
| Polydimethylsiloxane (PDMS) | ~1 MPa | Insulating | Nanofiber coating for improved insulation/patterning |
| Conductive Components | | | |
| Nanofiber Carrier Polymer (polycaprolactone, cellulose acetate, poly(methyl-methacrylate), ethylene vinyl alcohol) | Varies | Negligible | Used in combination with carbon-based dopants below |
| poly(3,4-ethylenedioxythiophene) polystyrene sulfonate (PEDOT: PSS) | <100 MPa | >100 S/cm | |
| Vapor-Phase Polymerized poly(3,4-ethylenedioxythiophene) (VPP-PEDOT) | <50 MPa | >100 S/cm | Possesses increased flexibility due to nanofibrous nature |
| Additives | | | |
| Carbon-Based Dopants | — | <1 mS/cm | When added as dopant to varied polymers, did not usably improve conductivity |
| Dimethyl sulfoxide (DMSO) | — | — | Improves conductivity and hydrolytic stability when added to PEDOT: PSS |
| STEC-Enhancers | Did not notably improve mechanical or electrical properties of PEDOT: PSS | | |
| Silanes | — | — | Improves adhesion between electrode layers |

It is also possible to use of poly(3,4-ethylenedioxythiophene) (PEDOT) as the bulk conductive material due to its previously demonstrated incorporation in neural interfacing applications as an electrode coating for improved electrolytic charge transfer between the electrode and neural tissue. Anion doping of PEDOT is necessary to obtain high material conductivity; both the conductivity and the hydrolytic stability of the polymer can be tuned by changing the counter ion.

It is also possible to employ two different deposition methods and anion dopants of PEDOT according to the embodiments disclosed herein. In this regard, poly(3,4-ethylenedioxythiophene) polystyrene sulfonate (PEDOT: PSS) is an aqueous-deposited product that can be cast into solid films capable of bulk conductivity and sufficient electrolytic charge transfer. Vapor phase polymerized (VPP)

ponent is then exposed to the EDOT vapors as described previously, resulting in PEDOT polymerization directly surrounding the Nylon-6 nanofiber structure. This process can be coupled with advanced photolithography techniques to focus polymerization within the patterned electrode template.

C. Additives and Coatings

The addition of several additives and coatings serve various beneficial purposes in the embodiments disclosed therein and are described in detail below.

Carbon-based Dopants—As mentioned above, carbon-based dopants both within and concentrated on the outside of the nanofiber structure may be employed.

Parylene-C/PDMS—A coating of Parylene-C over the electrospun nanofiber (e.g., Nylon-6) mat prior to lithographic patterning processes may be provided so as to prevent seepage of the lithography solvents through the void space of the samples and thereby prevent patterning accuracy being compromised. Parylene-C is however a moderately stiff material (E=2,757 MPa) and thus may affect the mechanical properties of the final nanofiber-based product. Alternatively or additionally therefore, polydimethylsiloxane (PDMS) (E ~1 MPa) may be employed as a coating around the nanofiber structure so as to enable successful patterning, insulation and stability of the underlying nanofiber (Nylon-6) support layer.

Standard gold traces (thickness 400 nm) can be deposited on top of the Parylene-C or PDMS-filled nanofiber substrate and subsequently encapsulated within additional insulation to create an electrode with a moderate improvement in mechanical flexibility (EMod ~2.5 GPa) due to the implementation of the nanofiber substrate.

Silanes—A variety of silanes, such as (3-glycidoxypropyl) trimethoxysilane (GOPS) and/or (3-aminopropyl)triethoxysilane (APTES) may be employed so as both the insulating and conductive layers to increase adhesion between layers and improve long-term mechanical stability of the electrodes.

DMSO in conductive layer—The addition of dimethyl sulfoxide (DMSO) to PEDOT:PSS films may be employed as a technique to improve conductivity. Commercially available aqueous PEDOT:PSS (Ossila Ltd.) having a sheet resistivity of 300 Ω/sq may be employed with an additional 5% (v/v) DMSO added prior to casting. Conductivity values nearly four times greater with DMSO-doped PEDOT:PSS (883 mS/cm) as compared to undoped PEDOT:PSS (250.76 mS/cm) may be achieved.

STEC enhancers—Several stretchability and electrical conductivity (STEC) enhancers may optionally be included in aqueous PEDOT:PSS films, such as bis(trifluoromethane) sulfonamide lithium salt, 4-(3-Butyl-1-imidazolio)-1-butanesulfonic acid triflate and/or 1-butyl-3-methylimidazolium octyl sulfate. STEC enhancers have been demonstrated to weaken the interaction between PEDOT and PSS to improve connectivity between PEDOT domains.

D. Single Layer Systems

Figure 3A:
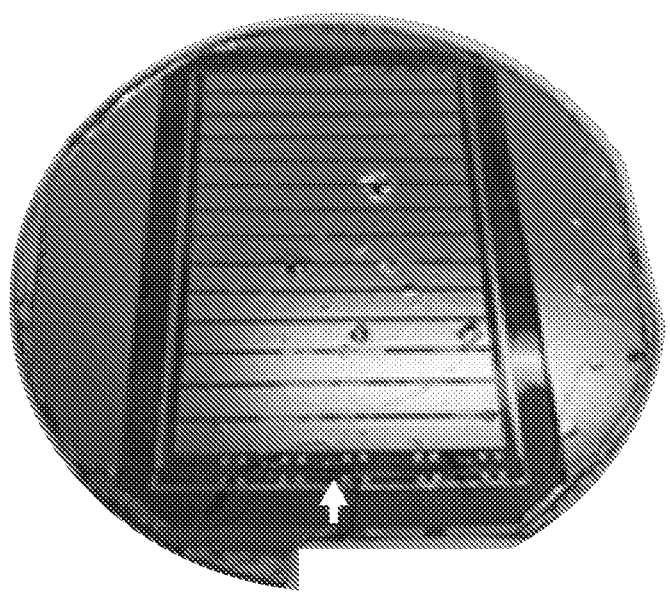
FIGS. 3A and 3B are photographs demonstrating poly (dimethylsiloxane) (PDMS) etching process within a nylon-6 nanofiber mat.
Figure 3B:
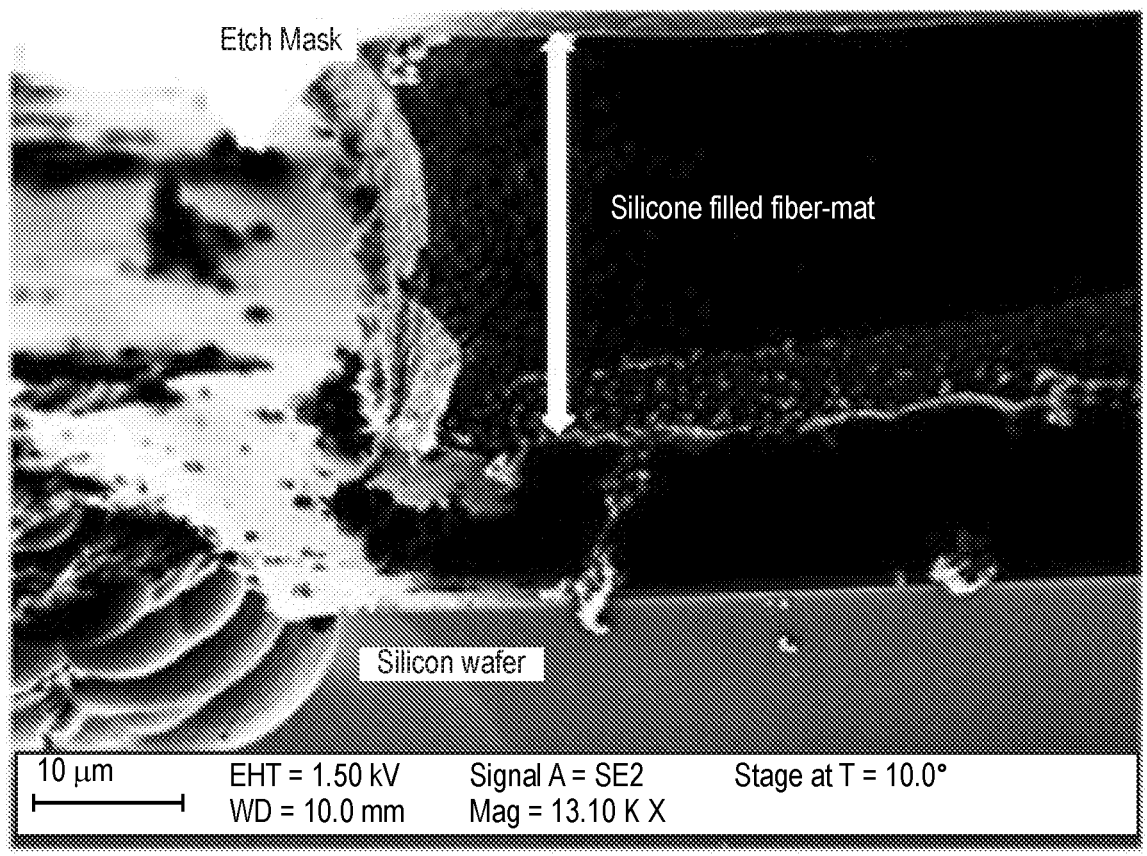

The technology disclosed herein may be embodied in a "single-layer" system in which the conductive polymer component is incorporated within the insulating nanofiber component, and the Parylene-C insulation is replaced entirely with poly(dimethylsiloxane) (PDMS). Incorporation of the gold or PEDOT conductive layer within the nanofiber substrate will prevent potential delamination and decrease thickness of the final product. While the embodiments described hereinabove employs two layers of Parylene C for electrical and lithographic insulation, it has been found that such an embodiment may be too stiff (e.g., with an elastic modulus of 3,460 MPa). PDMS, however, has an elastic modulus on the order of 1 MPa, which would enable further reduction in mechanical mismatch. PDMS incorporation in the nanofiber mat and subsequent etching is shown in FIGS. 3A and 3B.

Figure 4:
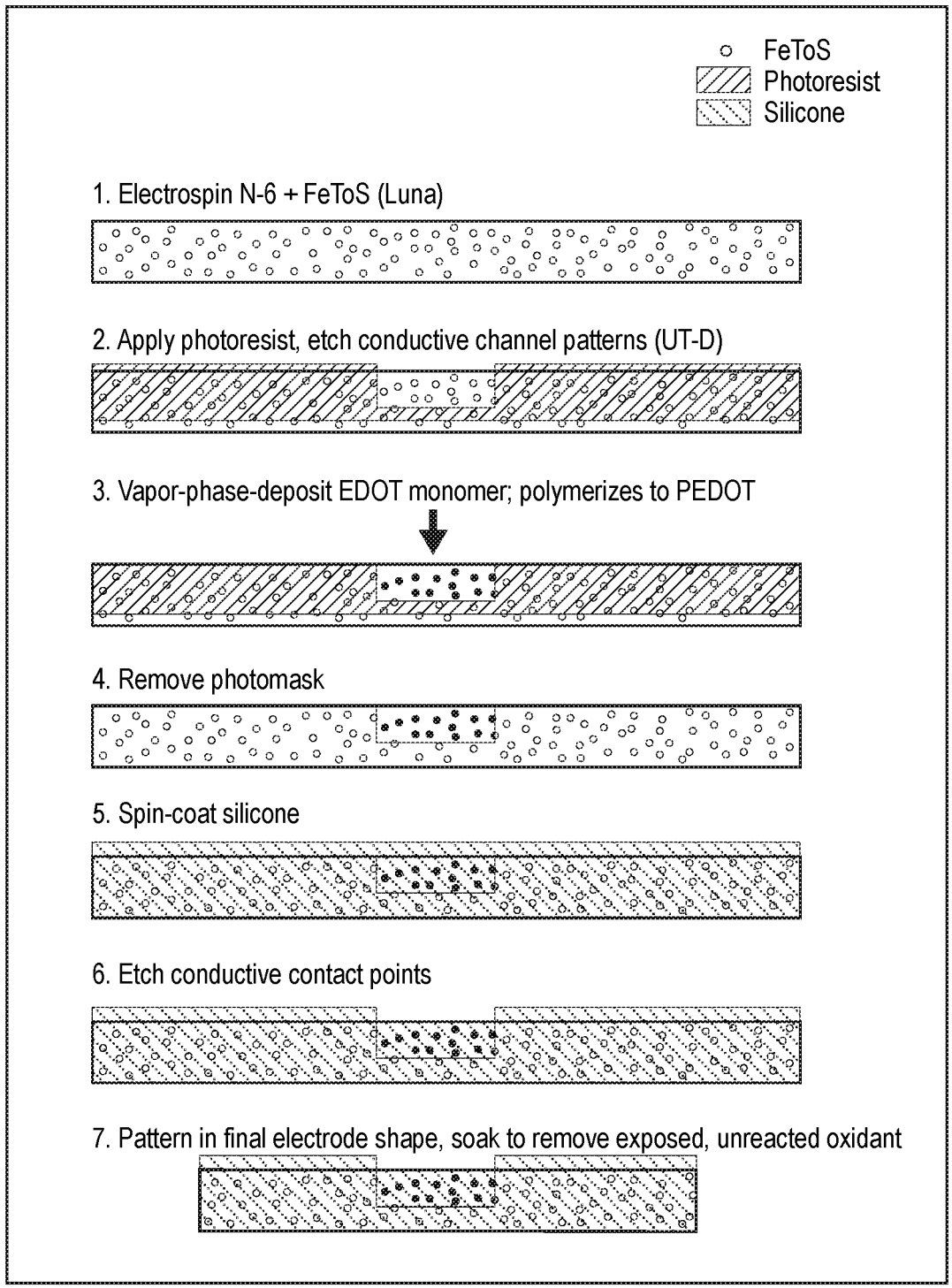
FIG. 4 depicts a sequence according to one embodiment for forming a single layer electrode.

The single layer electrodes may be fabricated by co-electrospinning Nylon-6 nanofibers and iron toluenesulfonate (FeTos) oxidant for VPP PEDOT, as depicted in the production sequence of FIG. 4. After electrospinning the combination Nylon/FeTOS nanofiber layer (Step 1 in FIG. 4), photoresist is applied and etched away from the conductive channel patterns (Step 2 in FIG. 4). The construct is then exposed to EDOT monomer for polymerization into the conductive channels, and the photomask is removed (Steps 3 and 4 in FIG. 4). The low PDMS viscosity allows a spin-coated application to enclose all sides of the PEDOT traces (Step 5 in FIG. 4), and conductive contact points can be etched in the PDMS (Step 6 in FIG. 4). The electrode is then patterned into the final shape and rinsed to remove exposed, unreacted oxidant (FeTOS) (Step 7 in FIG. 4).

Figure 5:
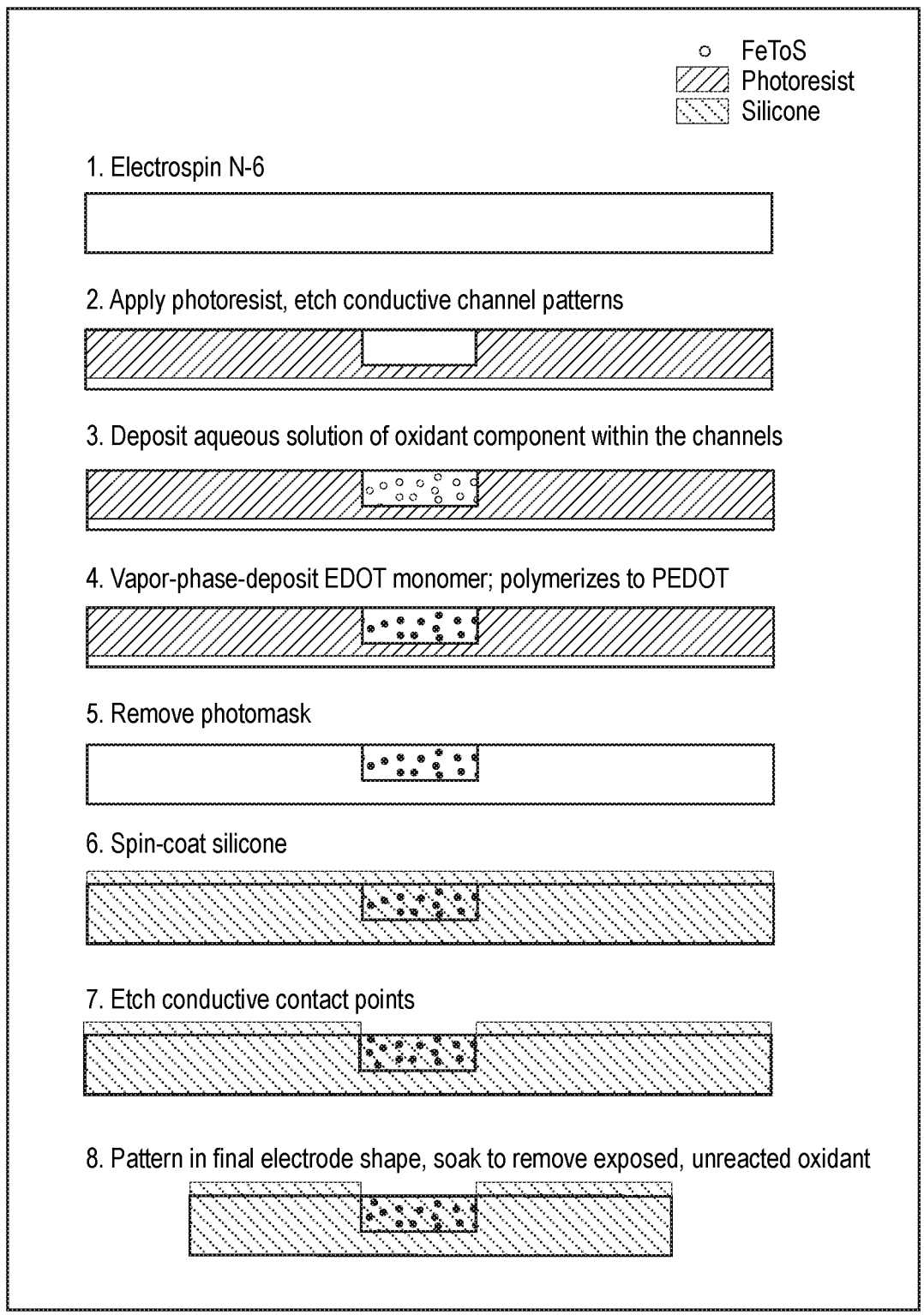
FIG. 5 depicts a sequence according to another embodiment for forming a single layer electrode.

Based on the preliminary stability issues with the oxidant component, an alternative electrode production process to enable rapid transition between the oxidant incorporation step and subsequent polymerization may be practiced as shown in FIG. 5. In this regard, Nylon-6 nanofiber mats are produced on the Cr-coated Si wafer, as discussed previously (Step 1 in FIG. 5). A photoresist (e.g., S1813 photoresist commercially available from the Shipley Company) may be applied throughout the mat and etched to form the electrode channel pattern (Step 2 in FIG. 5). Aqueous solutions/dispersions of the oxidant components (FeTOS, FeCl$_3$, or APS) are deposited on top of an electrospun nanofiber mat, and excess oxidant is removed using the spin coater (Step 3 in FIG. 5). The sample is dried and immediately transferred into the vapor phase polymerization chamber with EDOT vapor under vacuum to induce polymerization for 5 days (Step 4 in FIG. 5). The photomask can then be removed (Step 5 in FIG. 5), leaving PEDOT within the channels, and PDMS will be deposited around the conductive trace (Step 6 in FIG. 5). Contact points will be etched (Step 7 in FIG. 5) and the final electrode will be patterned and removed (Step 8 in FIG. 5).

Figures 5A, 5B:
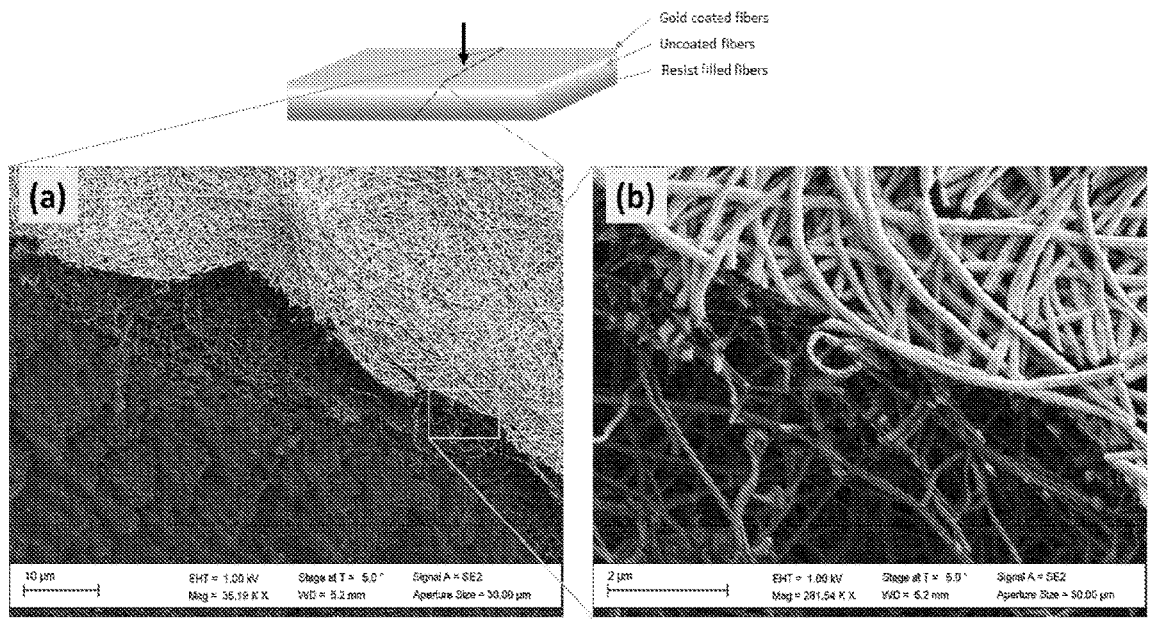
FIGS. 5A-5D are SEM photographs at different magnifications of an oblique cross-section of a nanofibrous substrate mat with electrically conductive traces in accordance with an embodiment of this invention.
Figures 5C, 5D:
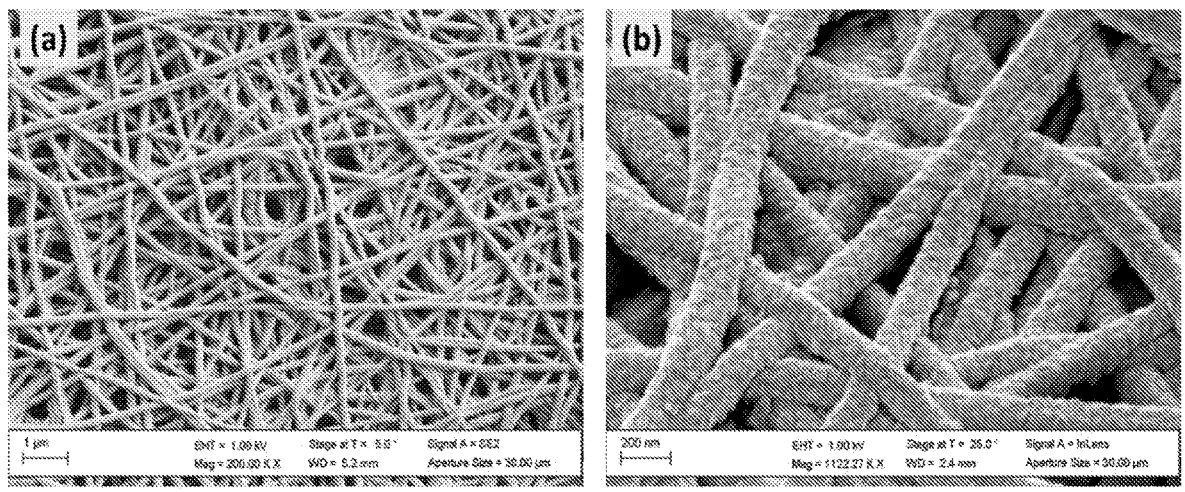

An alternative form to create a nanofibrous electrode trace includes the deposition of titanium (30 nm) and gold (100 nm) over the nanofiber substrate by metal evaporation. An oblique cross-section view of the fiber mat exposes all the layers in steps under SEM as shown in FIGS. 5A and 5B. The top surface of the fiber mat shown in the upper part of FIG. 5A depicts the metal-coated fibers, while the bottom part of FIG. 5B depicts the bulk of the mat filled with photoresist. Under the higher magnification of FIG. 5B, it is apparent that layers of uncoated nylon-6 nanofibers are visible underneath the top metal-coated fibers and can be clearly differentiated. The metal coated fibers appear brighter, rougher, and larger in diameter, owing to the deposition of ~130 nm of metal. Closer investigations on the surface of the metal coating shows evidence of a uniform coating on and around the top fibers, as seen in FIGS. 5C and 5D. The continuity of the metal and the lack of significant defects on the nanofiber surface appears promising for the fabrication of ultra-flexible, nanofiber-based electrodes. The use of a metallic conductive component would improve electrical properties as compared to PEDOT, and its application as a nanofiber coating would improve mechanical properties as compared to the first generation electrodes in which a continuous sheet of gold was used as the conductive trace.

Figures 5E, 5F:
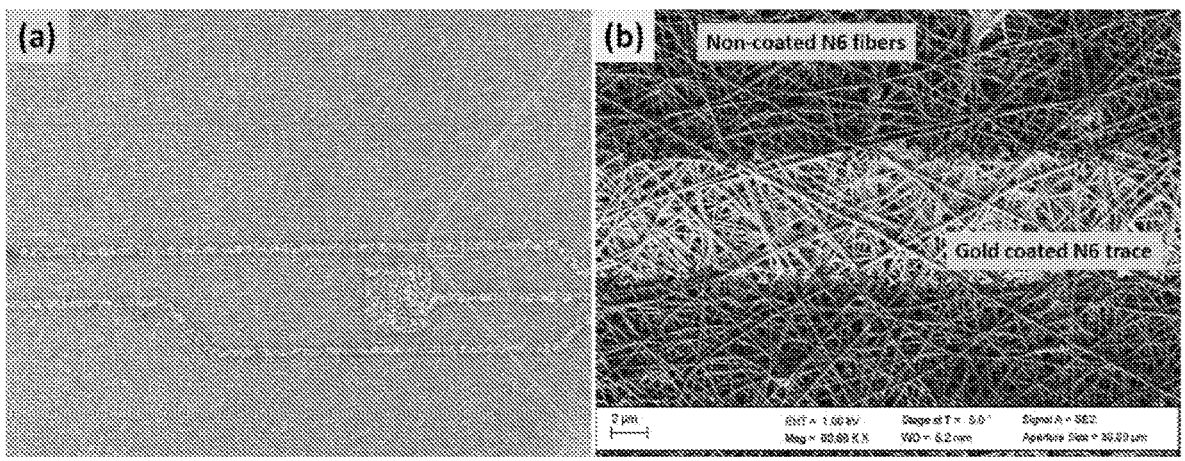
FIGS. 5E-5G are optical images of a patterned surface on a nanofibrous substrate mat at respectively increasing magnifications.
Figure 5G:
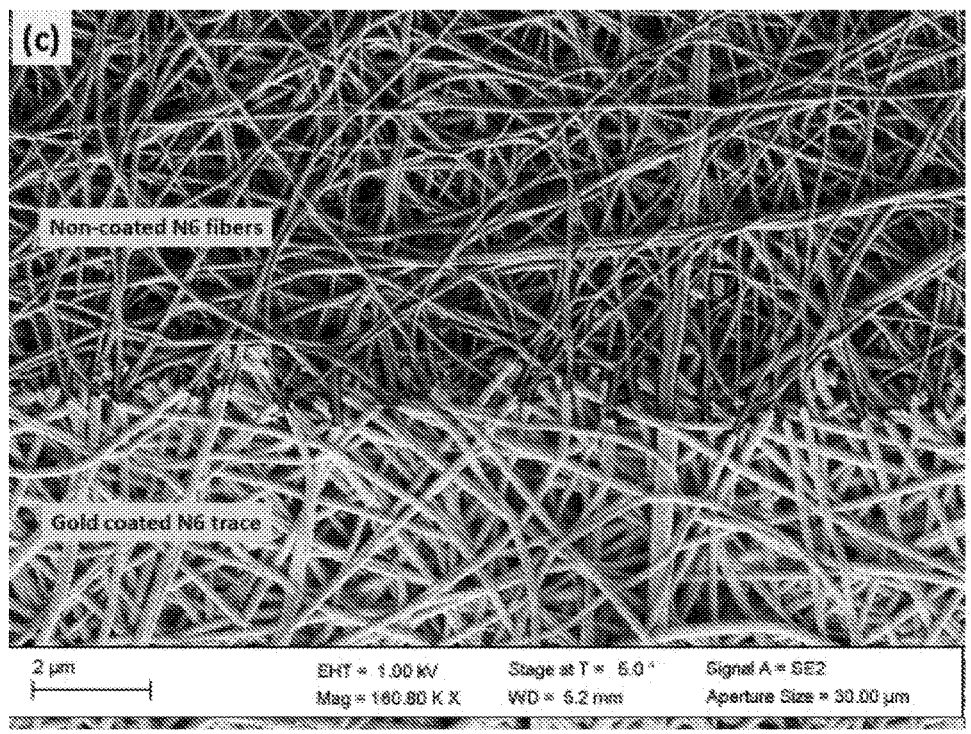

Following successful validation of gold deposition, the surface of the metal coating was patterned using the standard TIME electrode trace design. A fresh layer of photoresist was spin-coated on top of the metal-coated nanofiber mat, and wet chemical etching was used to transfer the pattern from the photoresist to the metal coating. The photoresist was then washed off by a soak and gentle agitation in acetone. FIG. 5E depicts an optical image of the patterned surface and shows that good definition of the pattern was achieved even in the narrowest traces of the design (~6 μm wide). FIGS. 5F and 5G present a very clear contrast between the metal-coated trace and the Nylon-6 nanofiber mat after metal etching. The nanofibers appear to retain their structure following photoresist removal. Preliminary electrical characterization of these samples confirmed the continuity of the metal coating. Electrodes fabricated using a gold coating over the Nylon-6 nanofiber substrate were found to be conductive with 1Ω resistance if measured 2.5 mm apart with a digital multimeter.

Figure 5H:
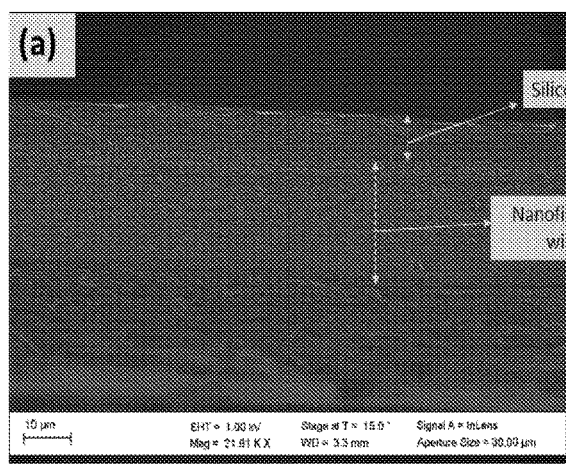
FIGS. 5H and 5I are SEM cross-sectional photographs of electrodes fabricated using a gold coating over a nylon-6 nanofiber substrate showing a silicone layer and a gold trace on a nanofiber layer filed with silicone, respectively.
Figure 5I:
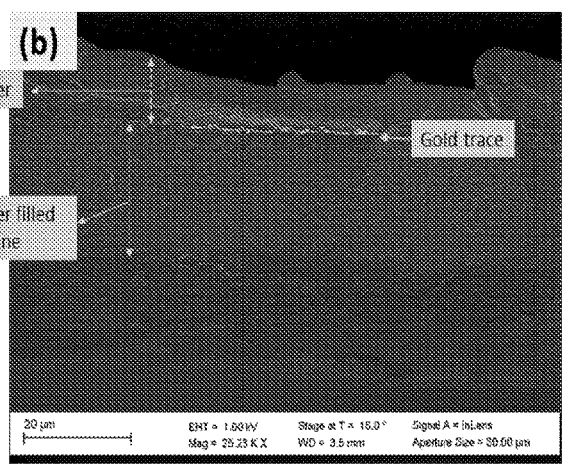

These devices were then filled with silicone dispersion. It was determined that the silicone successfully penetrated and filled the nanofiber mat successfully, despite the addition of the gold trace. FIG. 5H shows SEM cross-sectional views of the resultant samples, in which the nanofiber-silicone composite can be easily distinguished from the extra silicone coating on top of the sample. The thickness of this top silicone layer was reduced to approximately 5 µm, and the gold-coated nanofiber trace is clearly visible between this top silicone layer and the silicone-filled Nylon-6 nanofiber mat in FIG. 5I. Detachment of the silicone layer from the top of the gold-coated surface was noted, which will be addressed by depositing an additional layer of Titanium prior to silicone infusion.

The embodiments disclosed herein will be further understood by reference to the following Examples.

EXAMPLES

Device Characterization
A. Mechanical Characterization

In addition to maintaining appropriate electrical properties, it is important that the mechanical property mismatch between conductive materials and peripheral nerve tissue be reduced as much as possible. By way of example, metal wires currently utilized in conventional devices have elastic modulus of approximately 160,000 MPa, while nerve tissue is only approximately 0.6 MPa.

Figure 6:
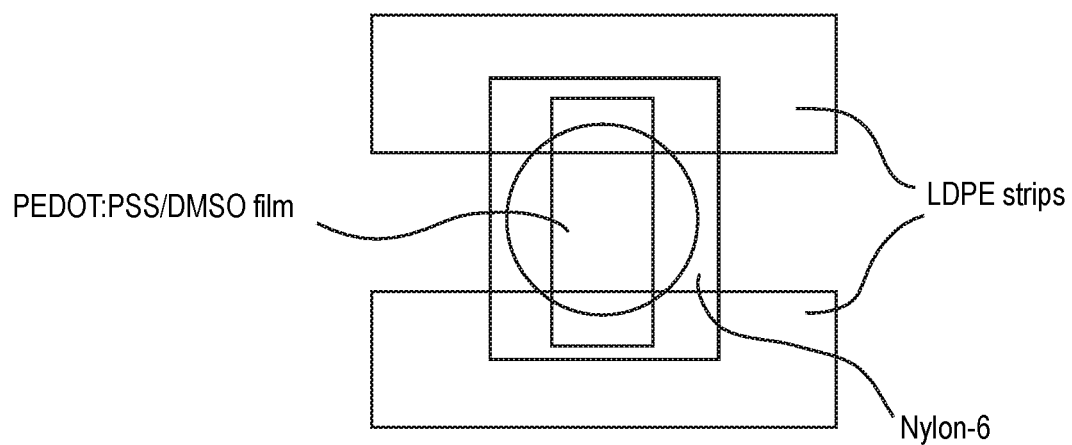
FIG. 6 is a schematic view of a mounting set-up for multi-layered samples of hydrated 1× phosphate buffered saline (PBS), with the area enclosed by chain line denoting an area of sample that underwent tensile testing per the examples below.
Figure 7A:
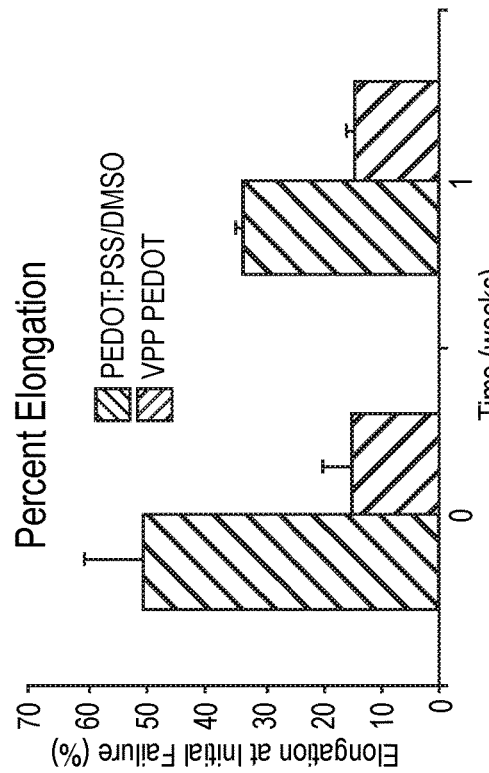
FIGS. 7A-7D are bar graphs depicting results of property testing for multi-layer samples of Nylon-6/PEDOT:PSS+ DMSO/Nylon-6 and Nylon-6/VPP PEDOT samples, at t=0 weeks (n=3) and t=1 week (n=3) of immersion in 1×PBS at 37° C., where
Figure 7C:
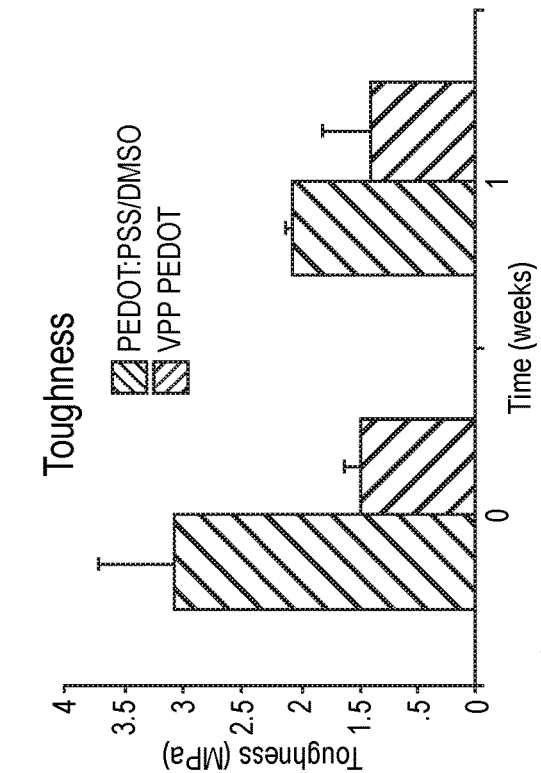
Figure 7B:
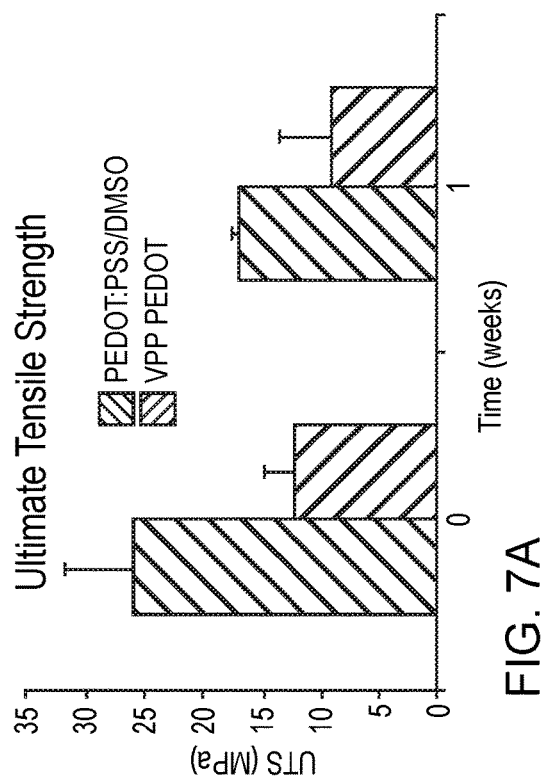
Figure 7D:
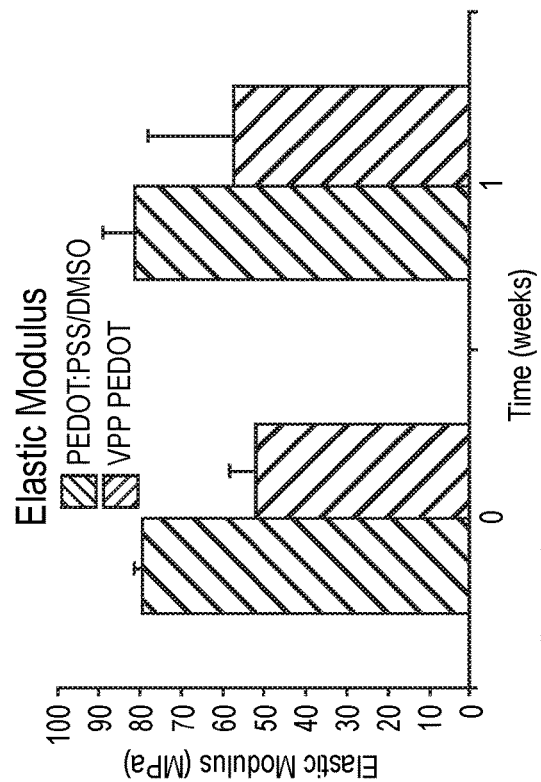
Figure 8A:
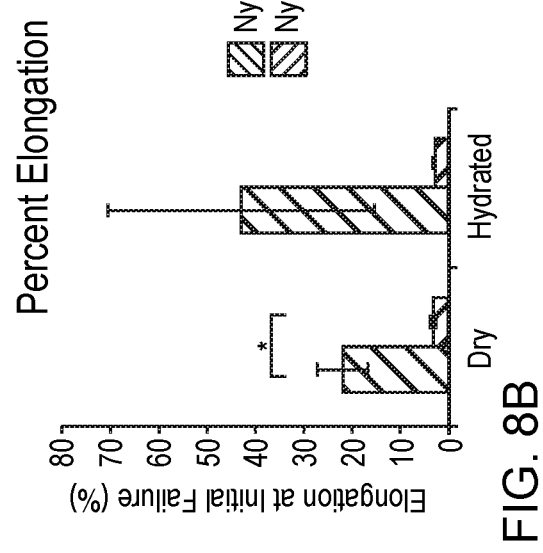
Figure 8B:
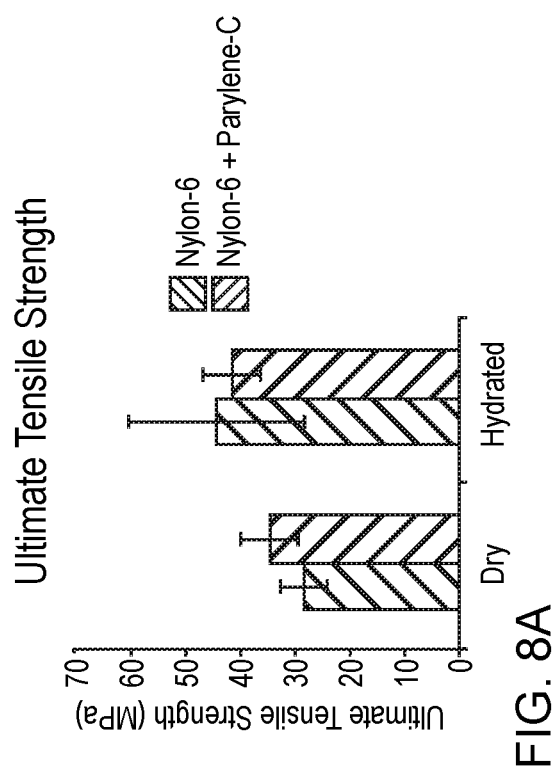
Figure 8C:
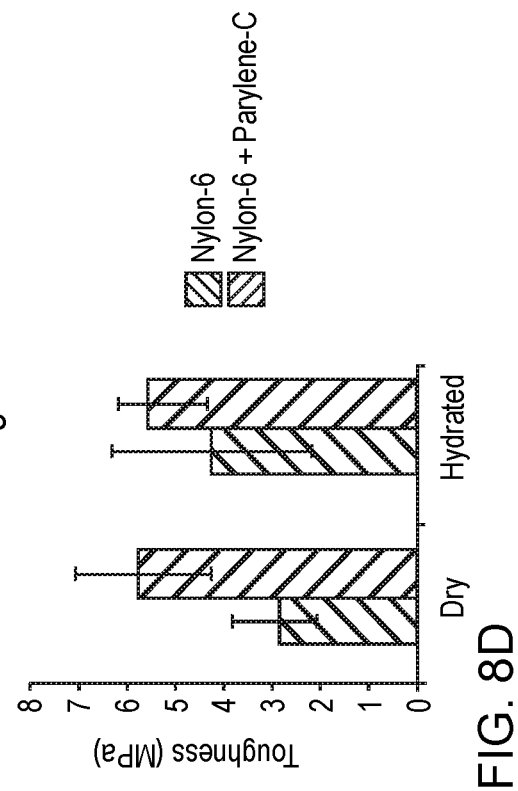
Figure 8D:
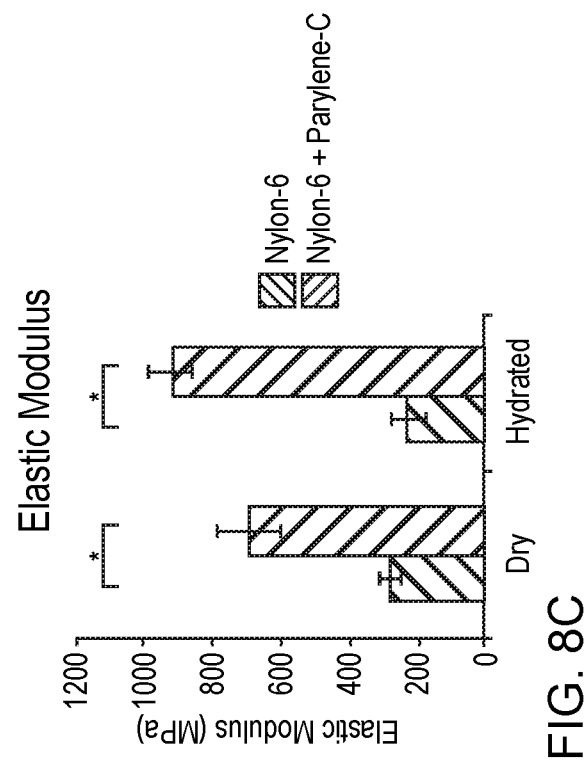

The mechanical properties of multi-layer Nylon-6/PEDOT samples using standard tensile testing protocols have been characterized. The thickness of each sample was measured with a digital thickness gage prior to sample mounting, and the width and length of each sample were measured with a digital micrometer. For ease of handling, samples were mounted at the tops and bottoms into 1×5 cm low density polyethylene (LDPE) frames (FIG. 6). Briefly, a dab of Loctite glue was placed on the top and bottom of each sample and the ends of each sample were placed to overlap the LDPE frames. Identical pieces of LDPE frame were placed over the lower frame and sample ends, sandwiching the samples between the two pieces of LDPE. Prior to tensile testing, samples were cut using an 8.45 mm wide cutting die to ensure uniform force transmission across a consistent area of 3-layer sample (area outlined in FIG. 6) during testing. The prepared sample assemblies were loaded into a high-precision Instron 5943 tensile testing setup with a 500 N load cell and pneumatic grips set at 70 psi. Samples were preloaded to 0.05 MPa to eliminate slack and tested to failure at a deformation rate of 5 mm/min. Luna first performed tensile testing on samples that had been immersed in 1×PBS at 37° C. for 0 and 1 week to investigate the effect of hydration on tensile properties such as tensile strength, percent elongation, toughness, and elastic modulus. Results are provided in FIGS. 7A-7D.

The average elastic modulus at 0 weeks for Nylon-6/PEDOT:PSS+DMSO samples was 77.77 (±1.50) MPa. After 1 week of immersion in 1×PBS, the average elastic modulus of the samples decreased insignificantly to 74.56 (±13.53) MPa. Ultimate tensile strength decreased over immersion time for the PEDOT:PSS+DMSO samples. Visual assessment and analysis of the stress-strain curves for these samples showed distinct failure of each of the individual layers in the midst of the testing protocol. While elongation at failure slightly decreased over the 1-week immersion, samples maintained elongation of 10% without failing, as would be required upon implantation.

Similar testing of Nylon-6/VPP PEDOT/Nylon-6 samples demonstrated average elastic moduli at 0 and 1 weeks of 51.91 (±6.70) and 57.34 (±20.91) MPa, respectively. These values fall within 2 orders of magnitude of native nerve tissue. The decreased modulus compared to PEDOT:PSS is indicative of the VPP PEDOT's flexible nanofibrous morphology. Additionally, the observed sample elongations of >10% lend further credence to the continued investigation of VPP PEDOT as a flexible conductive layer As mentioned above, the Parylene-C additive utilized for lithographic patterning control and electrical layer encapsulation is known to increase the stiffness of prototype samples, Therefore, tensile testing on Nylon-6 nanofiber mats coated in a 2-µm layer of Parylene-C was tested in comparison to an uncoated Nylon-6 nanofiber mat (FIGS. 8A-8D).

The elastic modulus of the Parylene-C coated Nylon-6 nanofibers was significantly greater than the elastic modulus of the Nylon-6 for both dry and hydrated samples. Additionally, the percent elongation at initial failure for the Parylene-C coated Nylon-6 was reduced to approximately 3% in both dry and hydrated cases. A mixed-contribution elastic modulus model for analysis of the Parylene-C-coated Nylon-6 nanofiber sheet based on the following formula has been developed:

$$E_{Total} = V_1 * E_1 + V_2 * E_2$$

where E is Young's Modulus, and V is volume fraction.

Since the sheet lengths and widths are uniform, the volume fraction term can be simplified to a thickness fraction. The model was created to estimate the tensile effect of the thinnest possible layer of Parylene-C on Nylon. Using this model, the measured results were initially compared to literature values of Parylene-C elastic modulus. From collected data, it was calculated a Parylene-C elastic modulus of 3,460 MPa, compared to literature values of 2,757 MPa. This suggests that the model will allow reasonably accurate approximation of the modulus of samples containing a thinner Parylene-C layer. It is postulated in this regard that a 1 µm Parylene-C layer is likely to be the thinnest layer capable of providing sufficient electrical and lithographic insulation. Inputting this thickness into the model, a hydrated elastic modulus of 692 MPa is predicted. This analysis confirms that the presence of Parylene-C makes the constructs stiffer and less elastic (though still significantly less stiff than currently used metal electrodes). By way of comparison a modeled 1 µm layer of amorphous silicon carbide provided a predicted elastic modulus of 41,989 MPa, far greater than that desired for this electrodes employed in the embodiments disclosed herein.

A. Electrical Characterization

The following table summarizes the analyses of electrical properties for devices in accordance with the embodiments disclosed herein:

| Analysis Type | Measured Property |
| --- | --- |
| Four-Point Probe Analysis | Bulk Material Conductivity |
| Cyclic Voltammetry | Material Stability, Charge-Transfer |
| Electrochemical Impedance Spectroscopy | Electrolytic Impedance, Phase Angle |
| Equivalent Circuit Model Fitting | Charge-Transfer Characteristics |

Bulk Material Characterization

Figure 9:
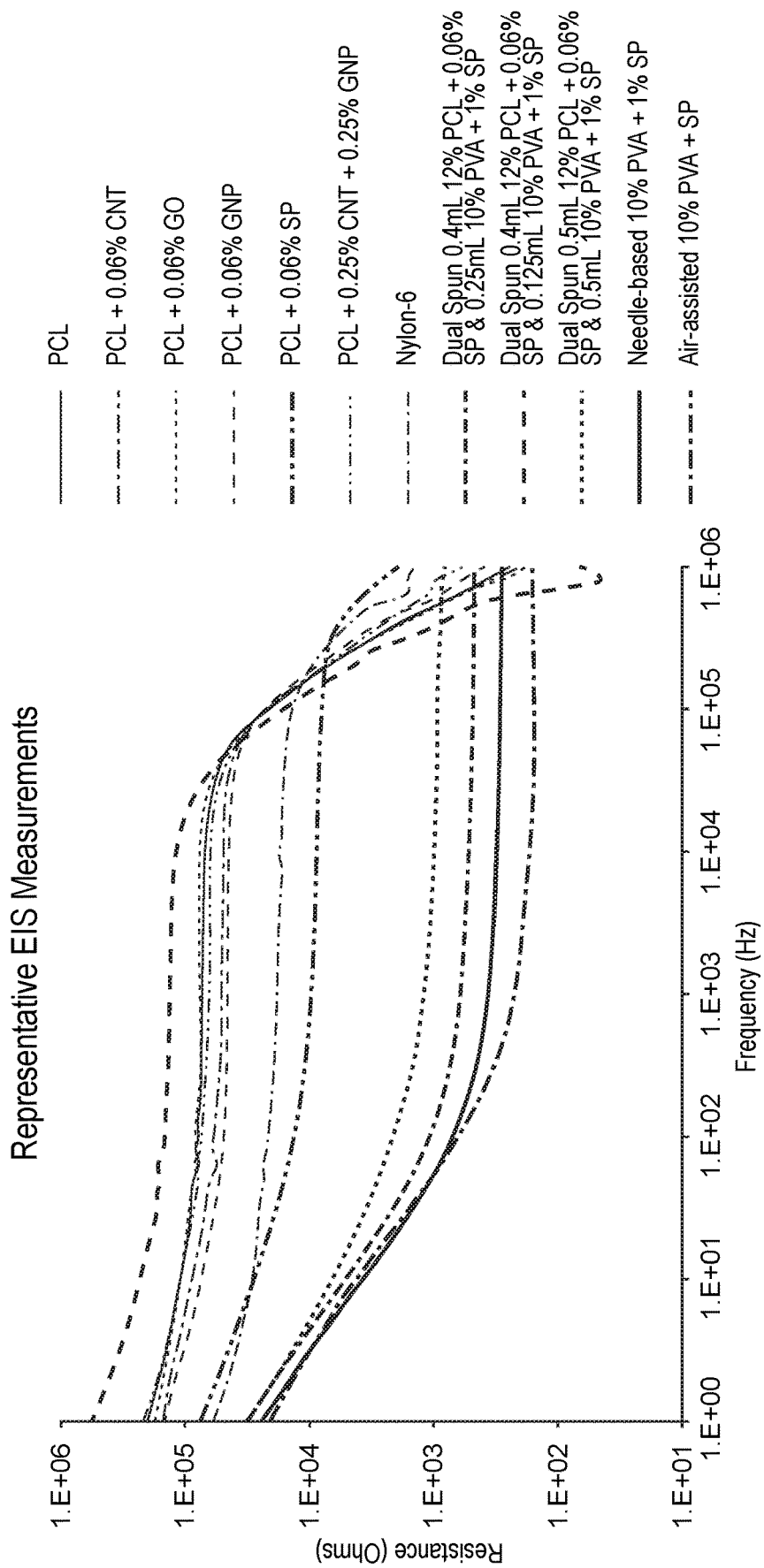
FIG. 9 is a graph of Resistance (ohms) versus Frequency (Hz) for various sample materials tested in the examples below.

Electronic property characterization of the material system using electrochemical impedance spectroscopy (EIS) has been performed so as to ensure that insulating chemistries were in fact insulating, and that conductive chemistries achieved conductivity profiles required for bidirectional communication with neural tissue. The resistivity of nanofibers was measured in order to assess changes in conductivity imparted by changing the bulk polymer, dopant chemistries, loading densities, sample thicknesses, and fabrication methods. For such characterization, samples were hydrated with a 10-150 µS/cm standard solution and placed on top of a 1 cm² gold interdigitated electrode sensor using a Gamry Interface 1000 electrochemical work station or a Biologic SP200 system. The EIS system then applied a sinusoidal voltage across the electrode to measure the responsive current wave and assessed the ohmic resistance and capacitance of the material. Over a range of <1 Hz to 1 MHz, a curve of measured impedance values can be generated to determine the conductivity of the sample in the region of interest. Impedance values were measured at applied frequencies from 1 Hz to 1 MHz with an applied AC voltage of 10 mV over an area of 10 cm², and resulted in curves seen in FIG. 9. Using a gold interdigitated electrode (IDE) calibration curve, these resistance measurements could be converted to bulk material conductivity values (mS/cm).

Due to the limitations of the EIS system in characterizing highly conductive samples, a Jandel four-point probe (FPP) system was also used for conductive layer characterization. Four-point probes operate by inputting and subsequently monitoring a DC constant-current signal through four equally-spaced micro-contact points. Current is passed between the outer points, while the potential drop between the inner two points is correlated to material resistance. Provided that the layer being measured is less than 5 mm thick and sample diameter is greater than or equal to 40 mm, the following equation:

$$Rs = 4.53\frac{V}{I}$$

where "V" is applied voltage, and "I" is applied current, is used to determine material resistance (Rs) in the special case of Ω/sq. Material resistivity (Ω*cm) and, by extension, conductivity (S/cm) is then determined by multiplying the sample resistance by the sample thickness. Measurements were conducted by placing a sample on a glass slide under the probe and lowering the probe head until it makes contact with the sample. A current, normally in the 10-100 µA range, was selected that allows adequate measurement of the voltage drop across the sample.

Figure 10:
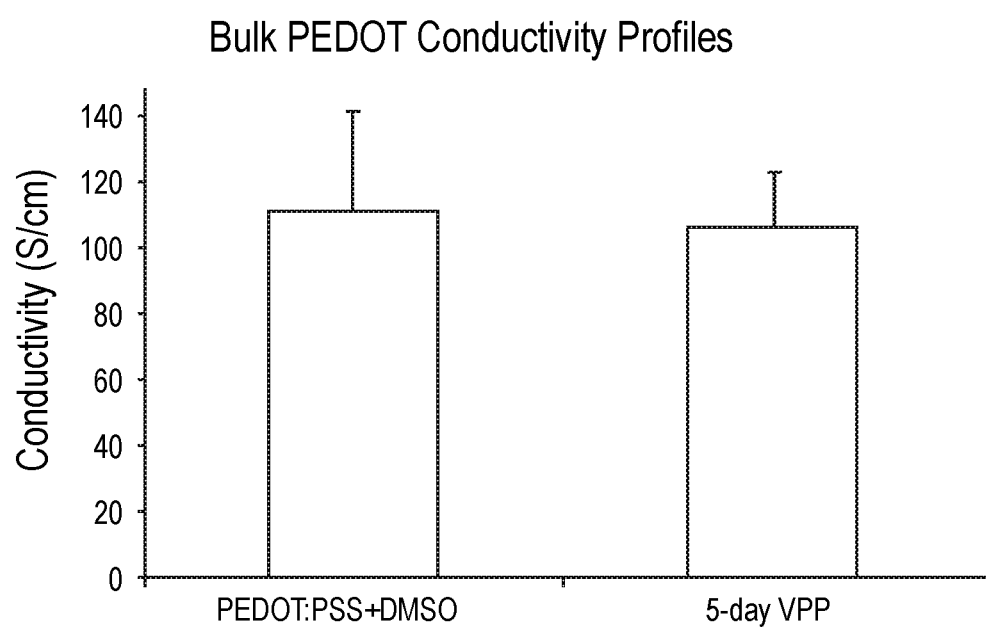
FIG. 10 is a bar graph showing Bulk Conductivities of two PEDOT conductive layer formulations according to the examples below.

Conductivity of both PEDOT conductive layer formulations, as well as Nylon-6 nanofiber mat were measured by a four-point probe. While the conductivity of Nylon was undetectably low, the two PEDOT formulations both achieved mean conductivities over 100 S/cm; well in excess of the calculated 35 S/cm necessary for use as an electrode material (FIG. 10).

Nanofiber Hydrolytic Encapsulation Capacity

Figure 11A:
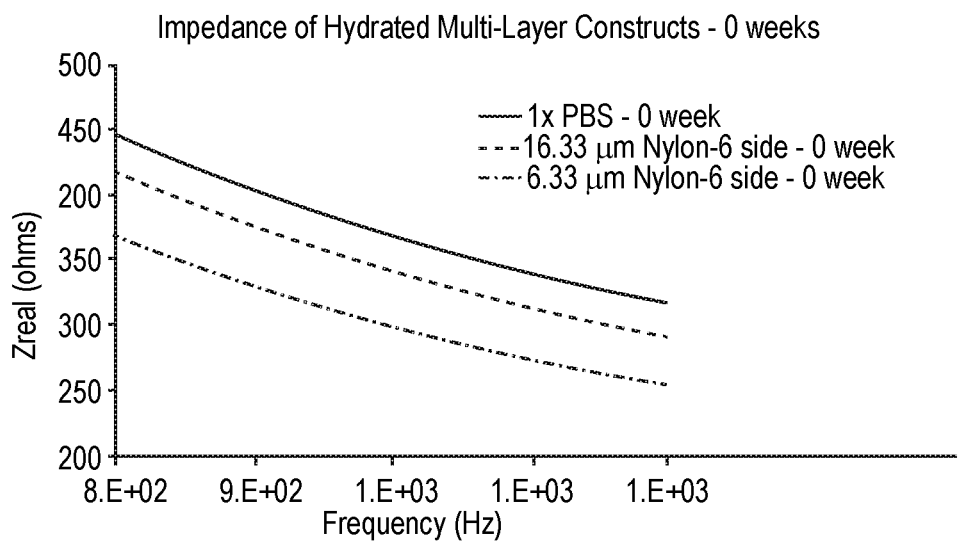
FIGS. 11A and 11B are hydrated EIS impedance spectra graphs of Zreal (ohms) versus Frequency (Hz) of hydrated multi-layer constructs at 0 weeks and 1 week, respectively.
Figure 11B:
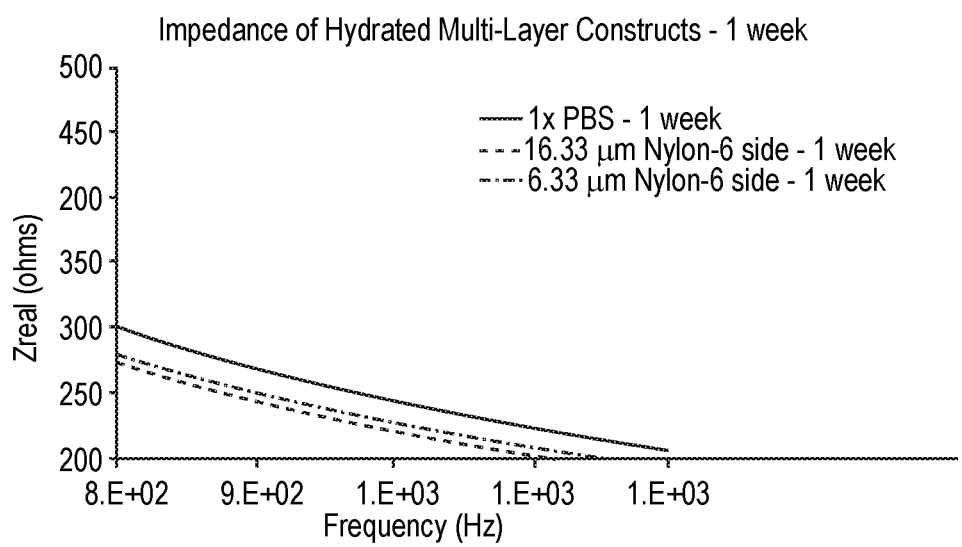

To investigate the ability of the Nylon-6 nanofiber mat to effectively encapsulate and insulate the conductive components, IDE-based EIS measurements of thick (16.33 µm) and thin (6.33 µm) hydrated (1-week immersion in 1×PBS) Nylon-6 nanofiber mats were acquired. Such data appears in FIGS. 11A and 11B. While the impedance spectra of both Nylon layers at t=0 suggests some encapsulation, impedance of both Nylon-6 construct layers decreased below that of PBS after being immersed in 1×PBS for 1 week.

Figure 12:
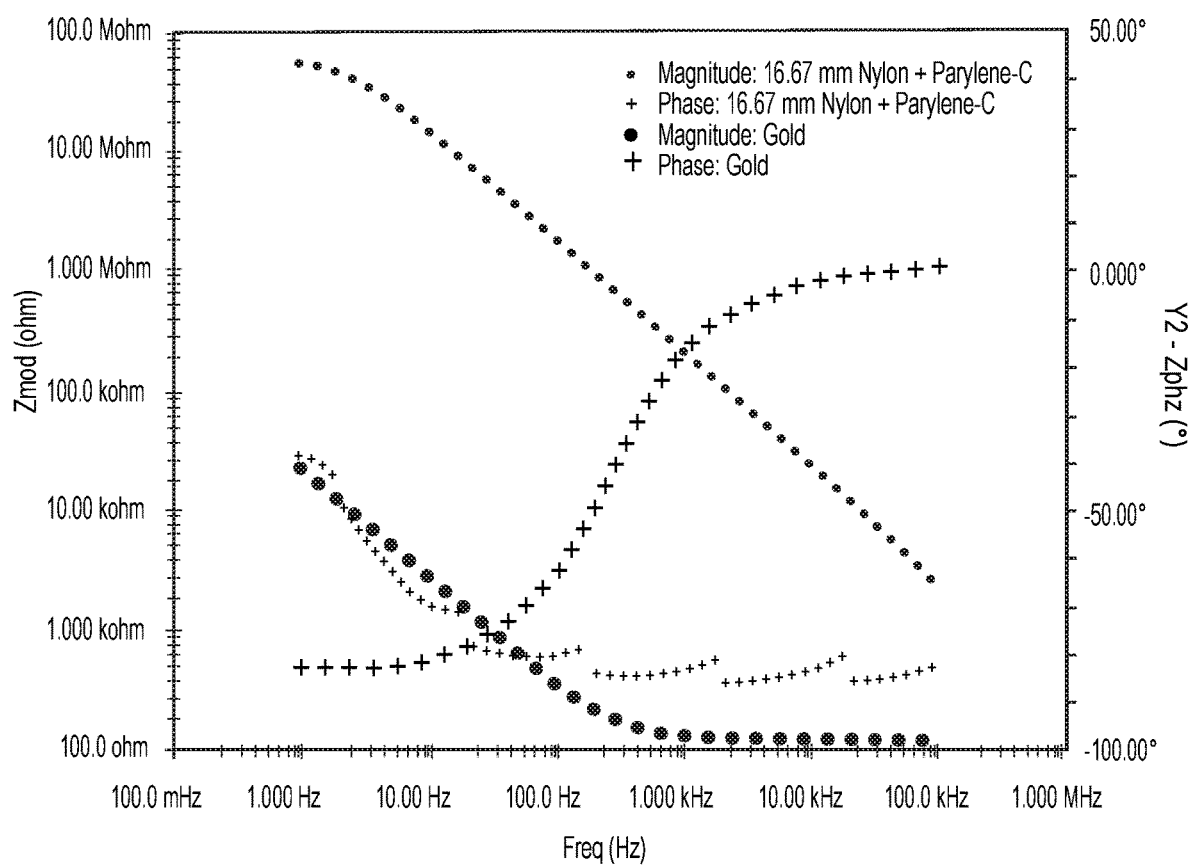
FIG. 12 is an impedance spectra of Nylon nanofiber sheet with Parylene-C layer and bar gold electrode.
Figure 13A:
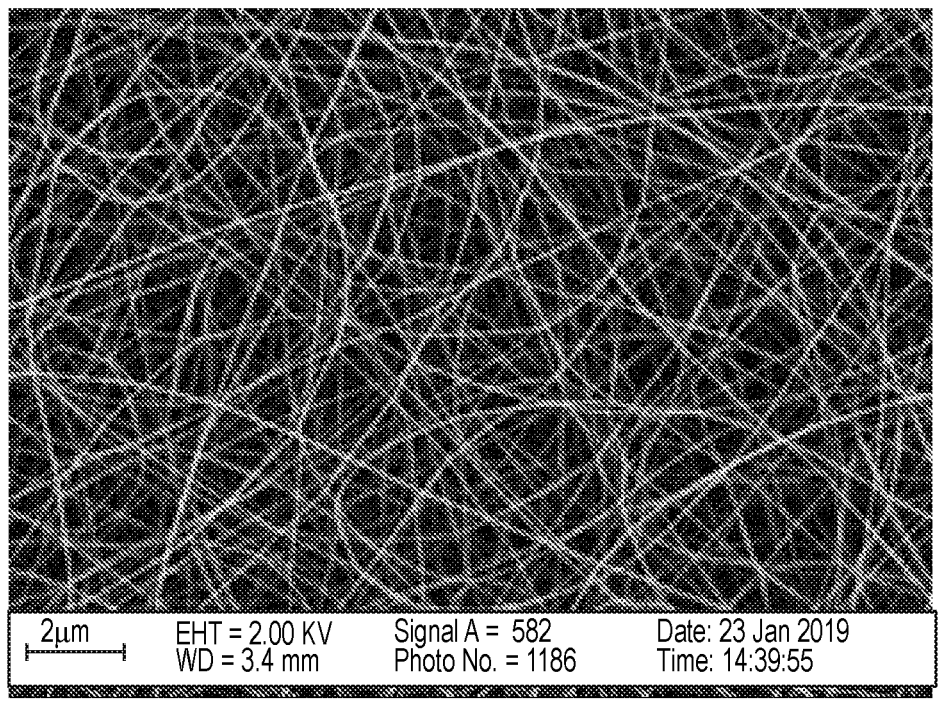
FIGS. 13A and 13B are scanning electron microscope (SEM) photographs of Nylon-6 nanofibers and Nylon-6 nanofibers with Parylene-C coating, respectively.
Figure 13B:
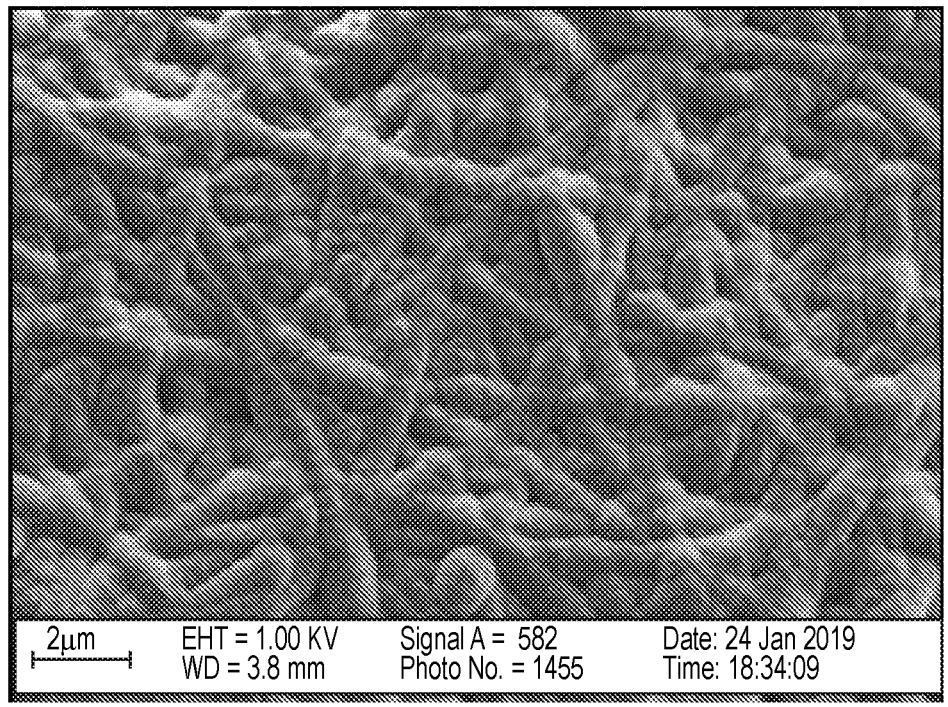

These results suggest that while the Nylon-6 provided partial insulation for the electrode at the 0-week timepoint, the electrical encapsulation was insufficient and essentially dropped to zero by the 1-week measurement. Based on these results, it was determined that the nanofiber mat required an additional insulating component. A relatively thin (1-2 µm) layer of Parylene-C was therefore incorporated as an insulating additive. As seen in the impedance spectra shown in FIG. 12, Parylene-C successfully insulates the nanofiber layer from electrolyte permeation, as seen by the shift between the red and black dotted lines. SEM images of Nylon nanofibers before and after Parylene-C deposition are also shown in FIGS. 13A and 13B, respectively. Beneficially, this layer application also improves lithographic patterning by filling voids within the nanofibrous material and preventing seepage of photoresist.

Electrolytic Charge Transfer Characterization

To further characterize the flexible neural electrode constructed according to FIG. 1, a 3-electrode electrochemical impedance spectroscopy (EIS) cell was configured for measuring electrolytic interface characteristics. The cell utilized the electrode's PEDOT conductive layer as the working electrode, a large platinum mesh as the counter (or auxiliary) electrode, and a BASi Ag/AgCl (3M NaCl) reference electrode. The electrolyte was 1×PBS, and the potentiostat was a Biologic SP200. Both electrochemical impedance spectroscopy (EIS) and cyclic voltammetry (CV) were performed. The basic operation of potentiostatic EIS involved holding the reference voltage constant while injecting current into the system at a range of frequencies (1 Hz to 100 kHz) and measuring the voltage transients at the working electrode. EIS describes the charge-transfer impedance and phase angle. CV involved scanning through a range of voltages (−0.5V to +0.5V) at a constant rate (10 mV/s). CV elucidates the charge-storage capacity and capacitance of a measured construct.

Figure 14:
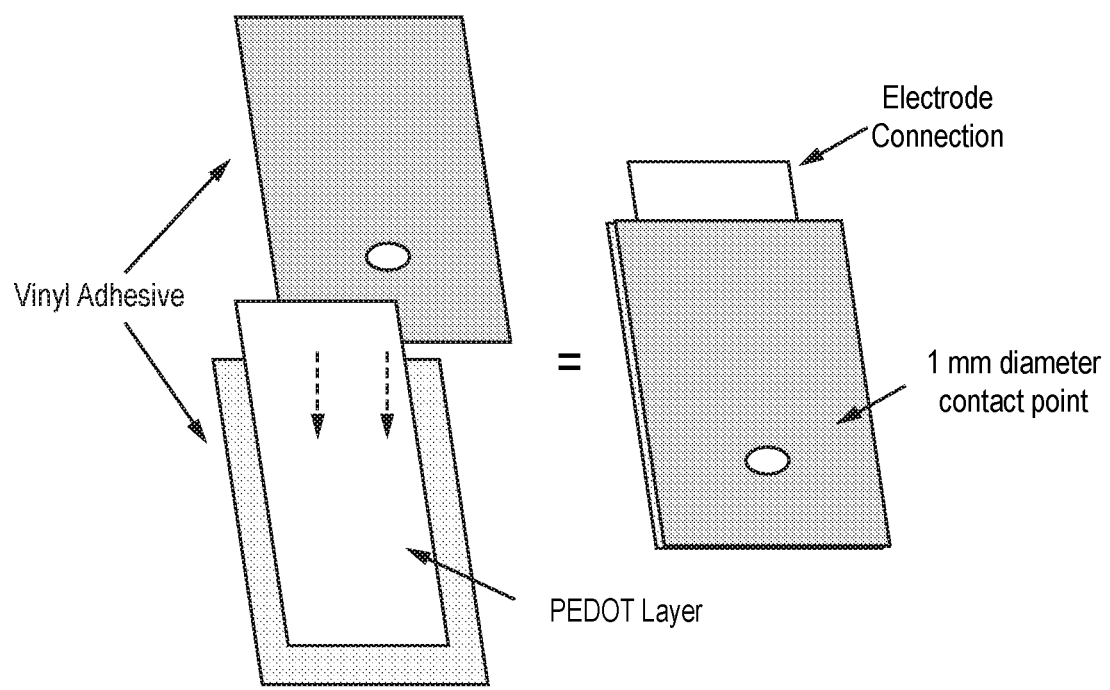
FIG. 14 is a schematic representation of vinyl patterns for PEDT electrode preparation.

To analyze these samples, the PEDOT was encased such that only a small area was left exposed to the electrolyte while sufficient material was exposed above the electrolyte level to permit electrode connection to the potentiostat. A vinyl cutter was used to create patterned vinyl stickers with a 0.5 or 1 mm diameter cutout for the electrode contact area. The patterned vinyl stickers were then applied around both sides of the PEDOT sample which insulated all immersed areas of the sample except the contact point. The arrangement for this testing is shown in FIG. 14.

Figure 15:
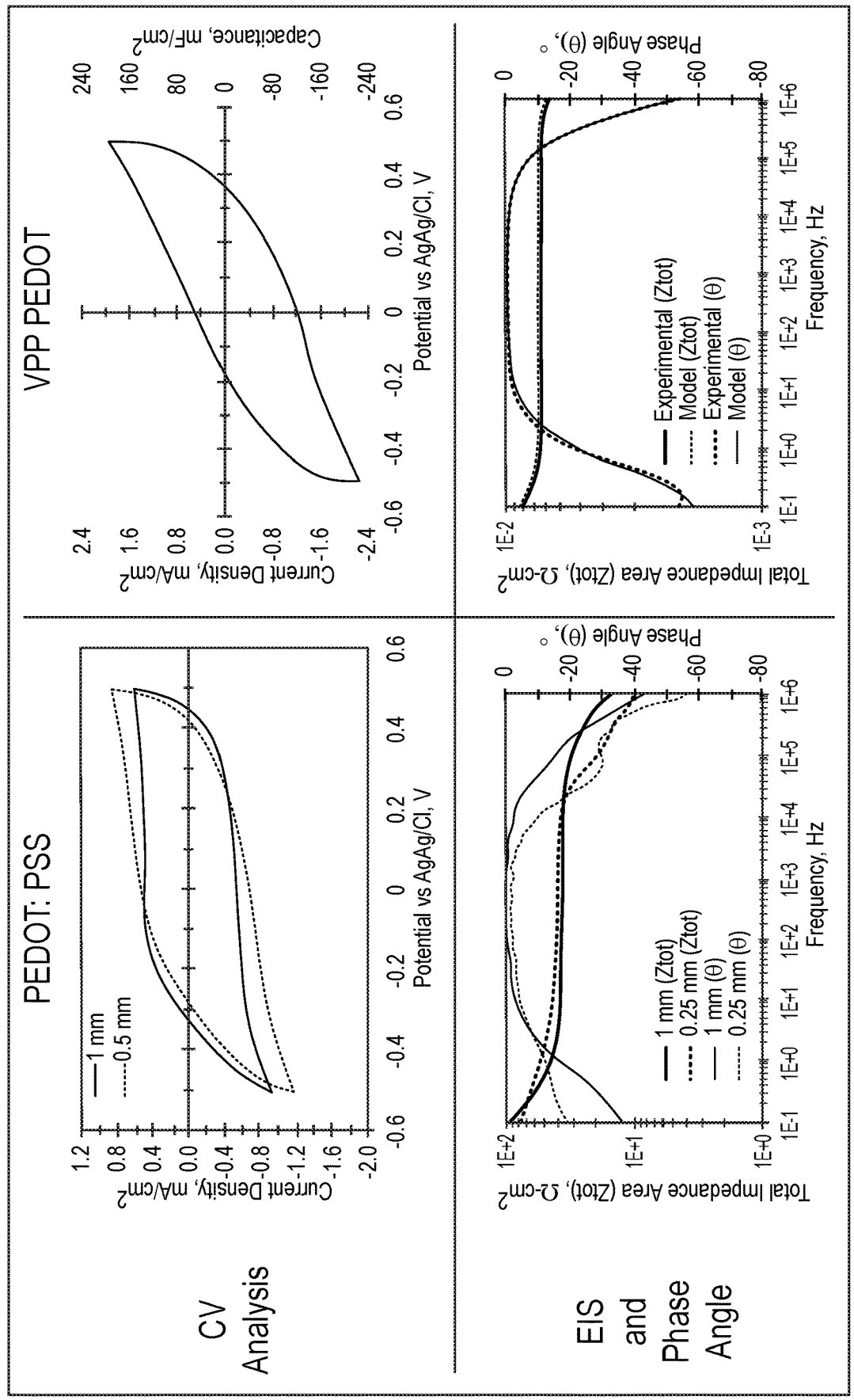
FIG. 15 are a series of electrochemical analysis graphs of PEDOT:PSS and VPP PEDOT materials.

CV and EIS were performed on both PEDOT:PSS and VPP PEDOT with 1 mm and 0.5 mm diameter electrode contact points. Data from the comparison is shown in FIG. 15. Both systems demonstrate both capacitive and pseudocapacitive behavior. According to equivalent circuit modeling, about 30% of the current response is contributed by true capacitance, and pseudocapacitive behavior contributes the remaining 70% of the current response. Assuming a 100 mV action potential output by a nerve, the PEDOT:PSS will produce a 5 mC/cm² signal or 0.1 µC for a 50 µm diameter nerve sensor area, while the VPP PEDOT will produce a 10 mC/cm² signal or 0.2 µC for a 50 µm diameter nerve sensor area. The increased capacitance of the VPP PEDOT as compared to the PEDOT:PSS is likely due to the significantly-greater exposed surface area due to the nanofibrous morphology of the substrate.

Sample Patterning

The electrode construct requires micron-scale patterning of the conductive portion of the electrode to enable interface with individual nerve fibers. In this regard, multiple methods of imparting macroscopic patterns into the electrospun nanofiber layers have been investigated, including stencil patterning, photopatterning, and photolithography. Stencil patterning was found feasible for larger-scale patterns (millimeters) but not for the micron-scale resolution required for the neural electrodes. Photopatterning, though feasibile, is not advisable due to the requirement for functionalization of the nanofiber chemistry, which is likely to significantly impact resultant conductivity. Therefore, photolithography is the currently preferred patterning method to achieve the electrodes of this invention.

Figure 16A:
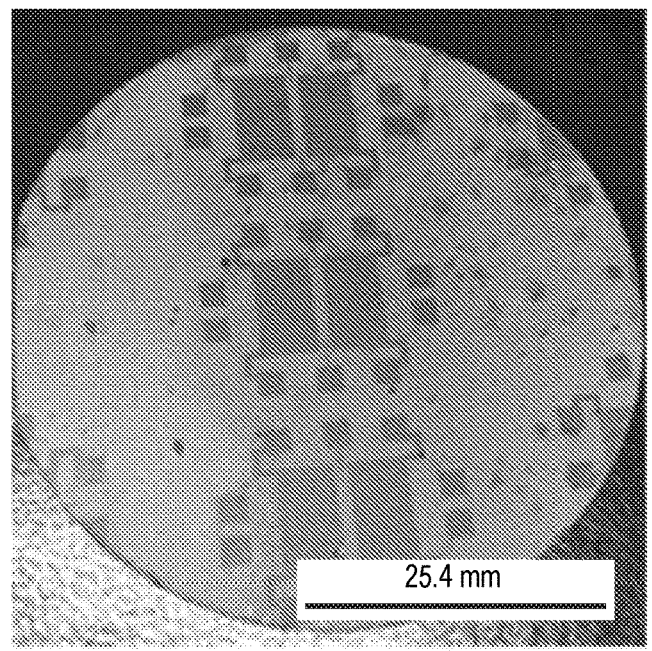
FIGS. 16A and 16B are photographic images of photolithography-processed samples.
Figure 16B:
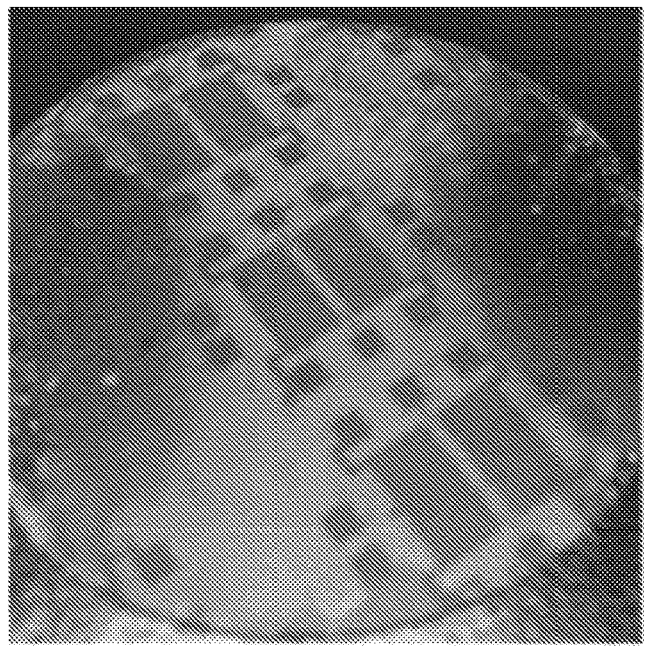

Preliminary patterning experiments were conducted to assess whether the chemistries being utilized were compatible with the solvents and processing conditions of photolithography as shown in FIGS. 16A and 16B. Some bubbling and sample burn was evident due to inefficient adherence of the samples to the silicon wafers, permeation of the solvents through the nanofiber layer, and suboptimal temperatures that "burn" the surface. Overall, however, basic compatibility of photolithography processing with these electrospun samples has been confirmed.

Figure 17:
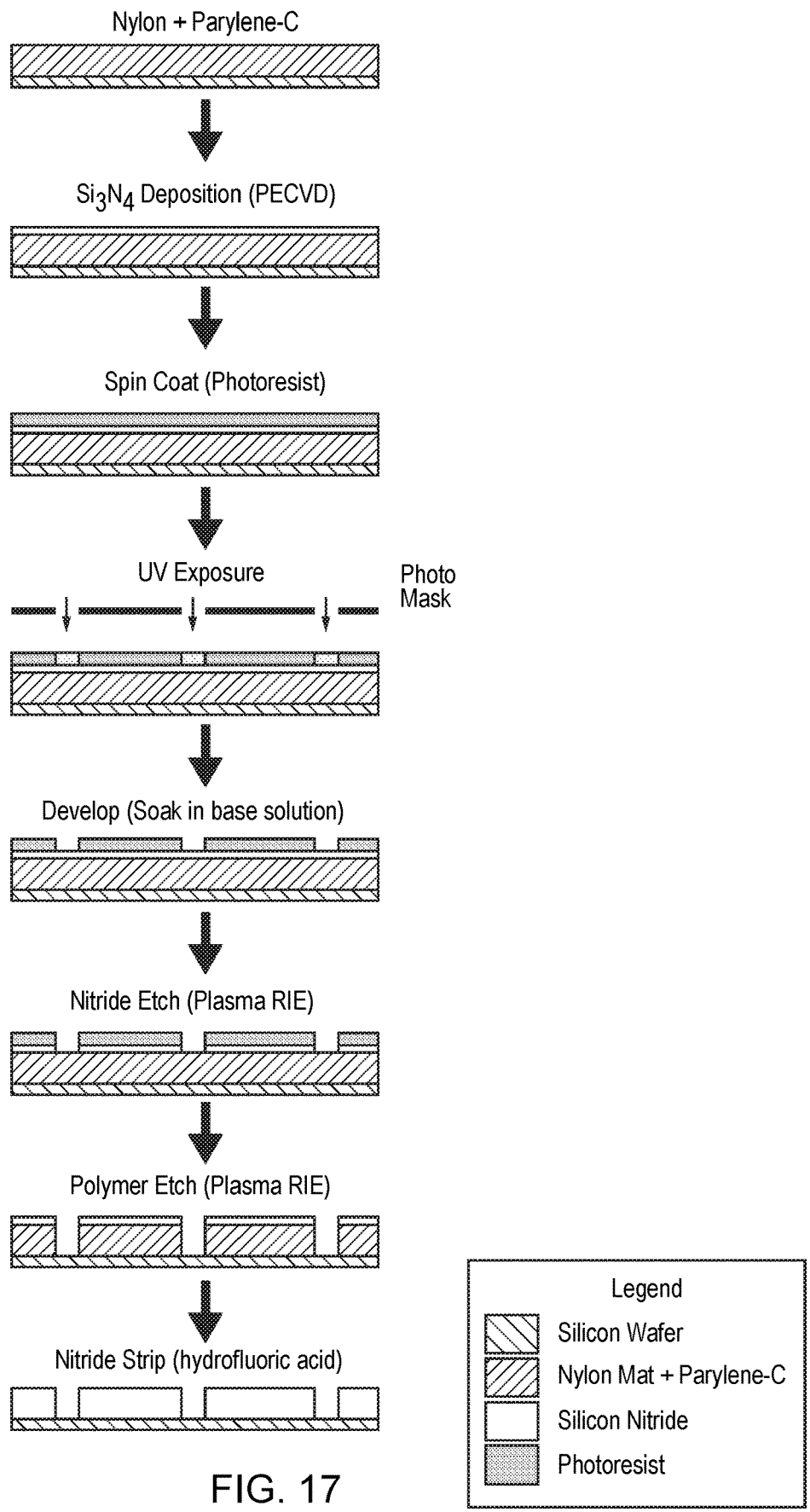
FIG. 17 is a schematic depiction of a sequence for a lithography procedure for patterning a Nylon-6 nanofiber mat.
Figure 18A:
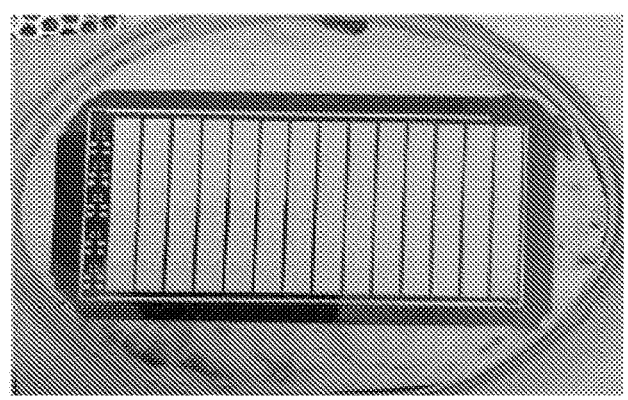
FIGS. 18A-18C are photographs showing the results of the sequence shown in FIG. 17 where
Figure 18B:
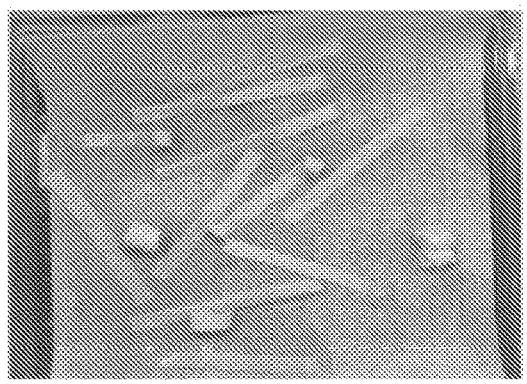
Figure 18C:
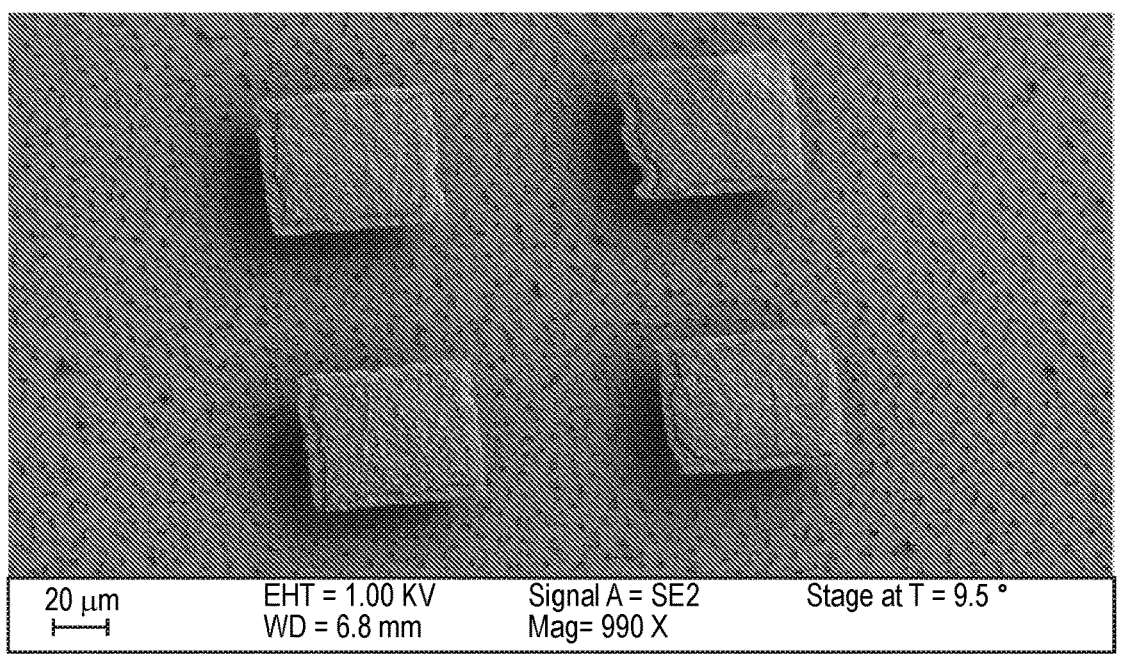
Figure 19:
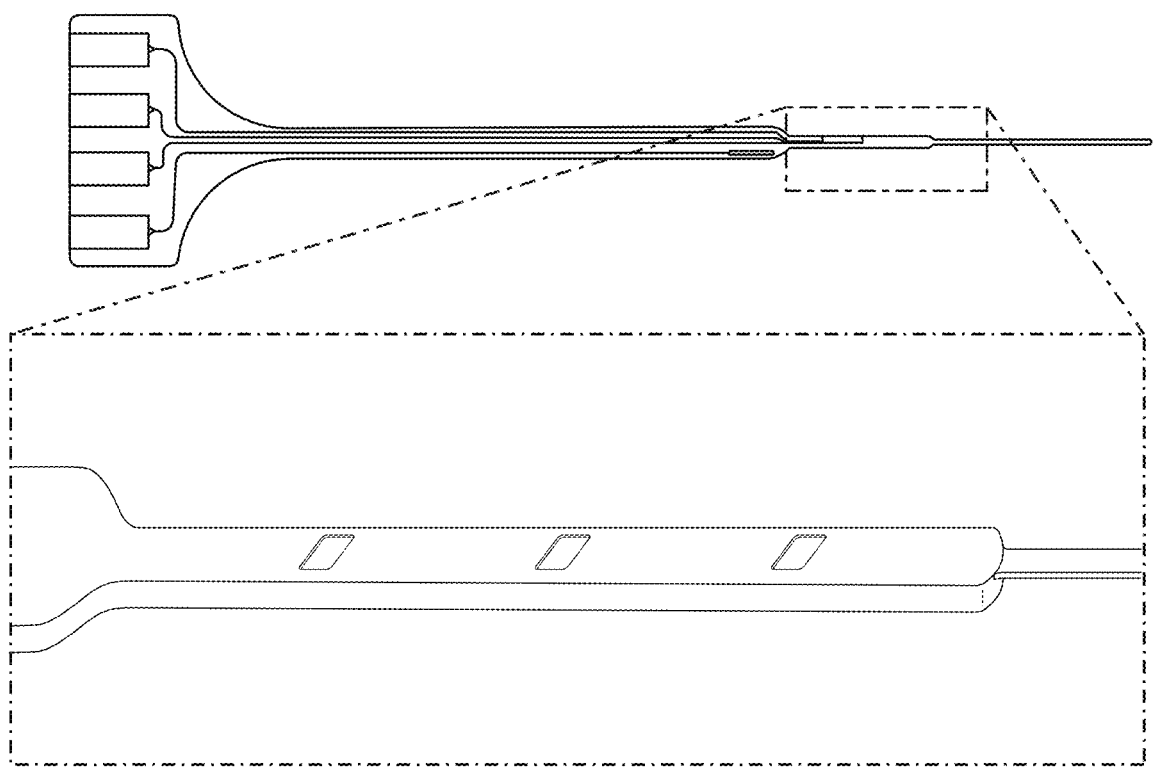
FIG. 19 shows a plan view illustrating a neural interface device in accordance with an embodiment of this invention and an enlarged SEM view of the etched electrode contact points thereon.
Figure 20A:
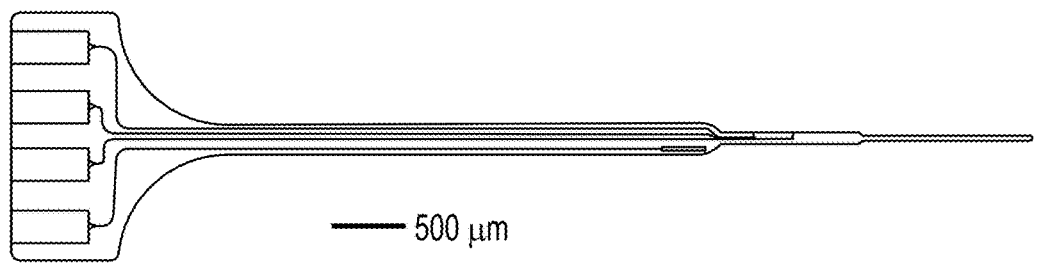
FIGS. 20A-20C respectively show a neural interface device in accordance with an embodiment of this invention in relation to a 500 μm scale (FIG. 20A), a scaled relationship of the device in FIG. 20A to a US penny (FIG. 20B) and a wafer containing multiple devices etched thereon (FIG. 20C)
Figure 20B:
Figure 20C:
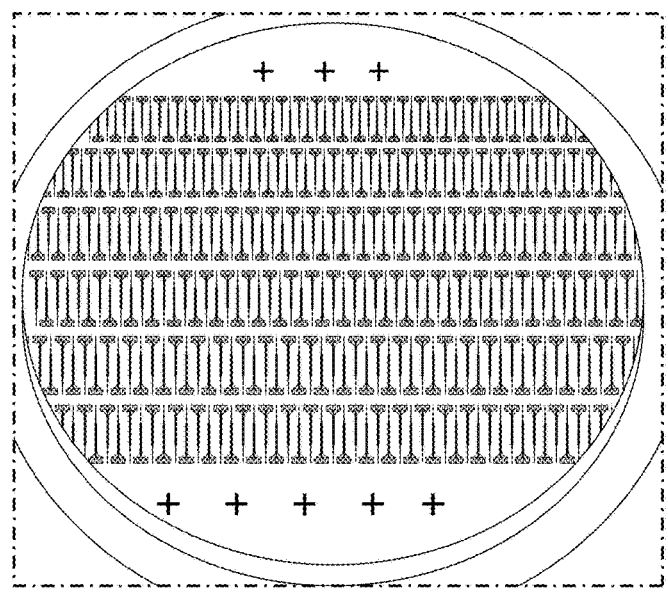

Nylon-6 nanofiber mats have been electrospun directly onto metal-coated silicon wafers to enable subsequent etching of the Nylon-6 layer using the procedure outlined in FIG. 17. As seen in FIG. 17, the Nylon-6 mat is first coated with a 1-2 µm layer of Parylene-C for enhanced insulation, stability, and improved patterning processes. The results of such a procedure as shown by the photographs of FIGS. 18A-18C.

To facilitate in vivo implantation, the neural electrode as shown in FIG. 1 was produced consisting of a Nylon-6 nanofiber substrate, a layer of Parylene-C, a 400 nm patterned gold conductive layer, and a top layer of insulating Parylene-C. Such electrodes exhibited significantly better as compared to conventional neural electrodes. Images of such electrodes are shown in FIGS. 19 and 20A-20C.

Figure 21A:
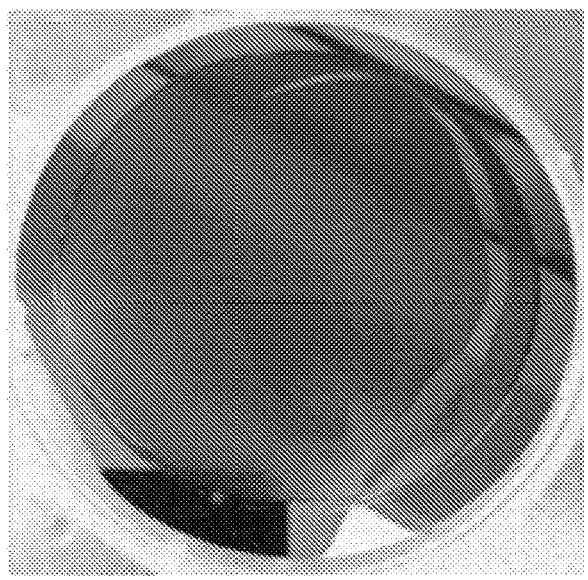
FIGS. 21A-21C are images of a PEDOT:PSS-coated silicon wafer after an annealing step and deposition of 205 nm SiN layer (FIG. 21A), completed photolithography with SU-8 resist and pattern transfer by reactive ion etching (FIG. 21B) and oxygen plasma etch of 6 μm PEDOT (FIG. 21C)
Figure 21B:
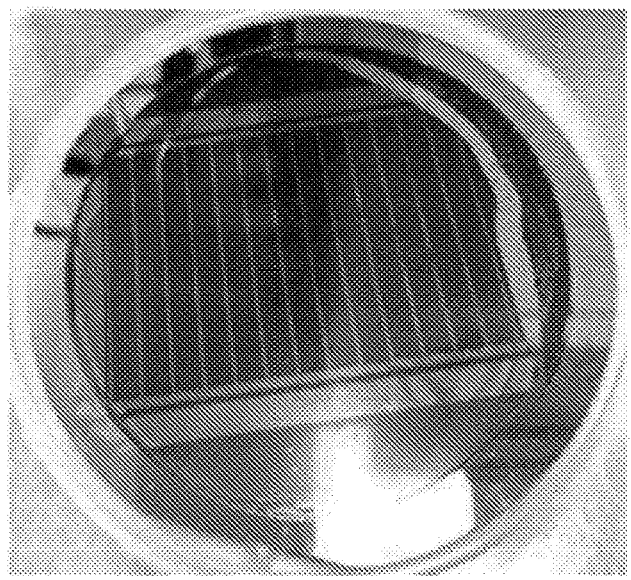
Figure 21C:
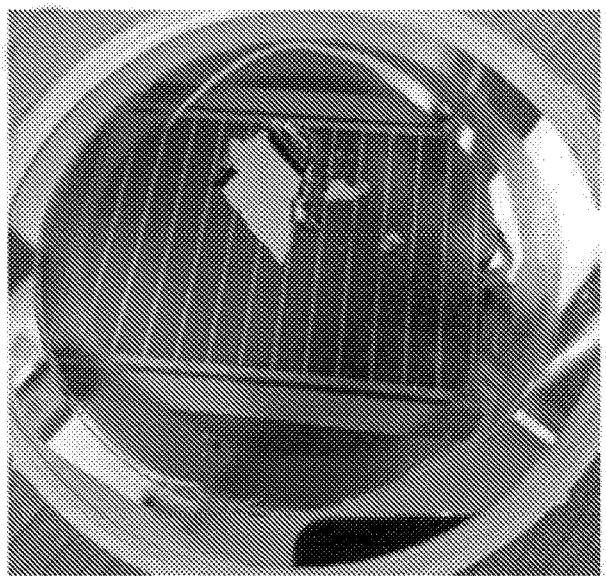

In order to use other solvents, the PEDOT:PSS film needs to be coated with a barrier layer (e.g., silicon nitride) to avoid direct contact. Silicon nitride deposition led to the formation of fissures and bubbles, therefore requiring alternative methods to be developed. The feasibility of annealing the PEDOT:PSS film at 150° C. prior to deposition of the silicon nitride, which can then be removed by dry etching using fluorine-plasma reactive ion etching has been demonstrated. Upon inspection, some PEDOT delamination was observed, so the full etch of 18 µm thickness was not completed. To alleviate this delamination, solvent compatibility of the cast PEDOT:PSS film was investigated, and isopropanol and acetone as compatible solvents were identified that did not delaminate the film. Solvents with any proportion of tetramethylammonium hydroxide (TMAH) decomposed the PEDOT:PSS film and hence cannot be used. FIGS. 21A-21C are images of a PEDOT:PSS-coated silicon wafer after an annealing step and deposition of 205 nm SiN layer (FIG. 21A), completed photolithography with SU-8 resist and pattern transfer by reactive ion etching (FIG. 21B) and oxygen plasma etch of 6 µm PEDOT (FIG. 21C)

Stability Characterization

Preliminary soak/stability testing by immersing prototype interface materials in saline has been demonstrated. The results of this experiment showed no significant changes in elastic modulus or peak tensile strength after one week. Qualitative analysis of long-term immersion of these preliminary samples showed no changes in structure or delamination with more than 6 months immersion Other efforts to characterize sample stability included the immersion of three-layer Nylon-6-encased PEDOT:PSS and VPP PEDOT samples in PBS for an extended time period. In addition to qualitative assessment of sample stability, the electrical and mechanical properties of these samples were characterized over time. Qualitative delamination of thinner (~16 micron) samples and subsequent degradation of the conductive layer in these samples were observed. Thicker samples (~32 micron) appeared to maintain improved stability in these preliminary characterization tasks.

Due to the potential issues associated with electrode delamination following implantation, the application of several silane additives within the PEDOT and Nylon-6 components has been investigated. The shear and normal forces of sheet adhesion has been tested to assess the adhesion of adjacent layers within the electrode (specifically between Nylon-6 layers encapsulating the patterned conductive layer). Modified versions of ASTMs D1876 and D3163 (T-peel and single lap-joint tests) were followed to assess the adhesion between two electrospun Nylon-6 mats.

Figure 22A:
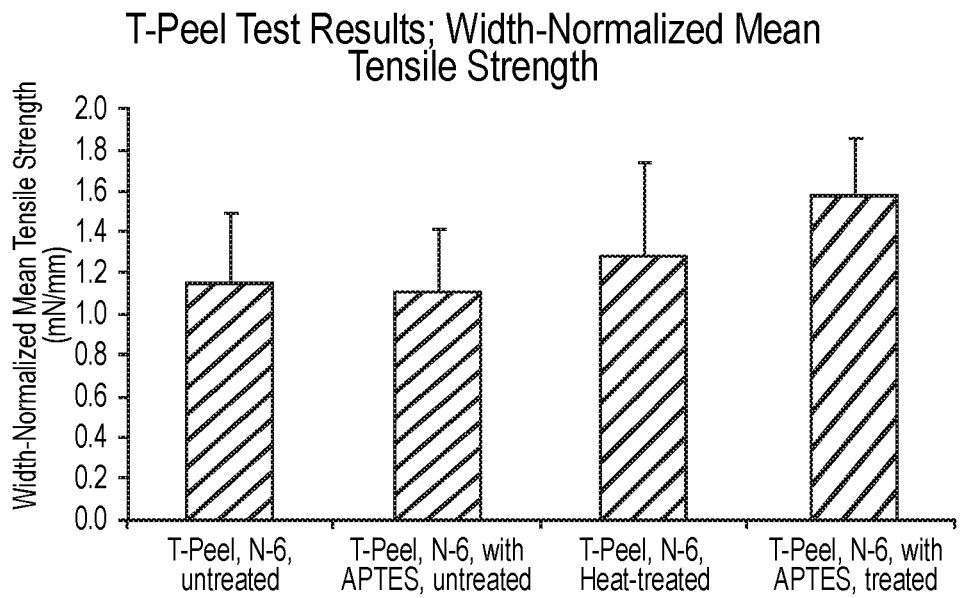
FIGS. 22A and 22B are bar graphs showing the test results from Nylon-6 nanofiber bilayer samples tested in T-peel (FIG. 22A) and single lap joint (FIG. 22B) tests to assess the effects of (3-aminopropyl) triethoxysilane (APTES) additive and post-processing heat treatments.
Figure 22B:
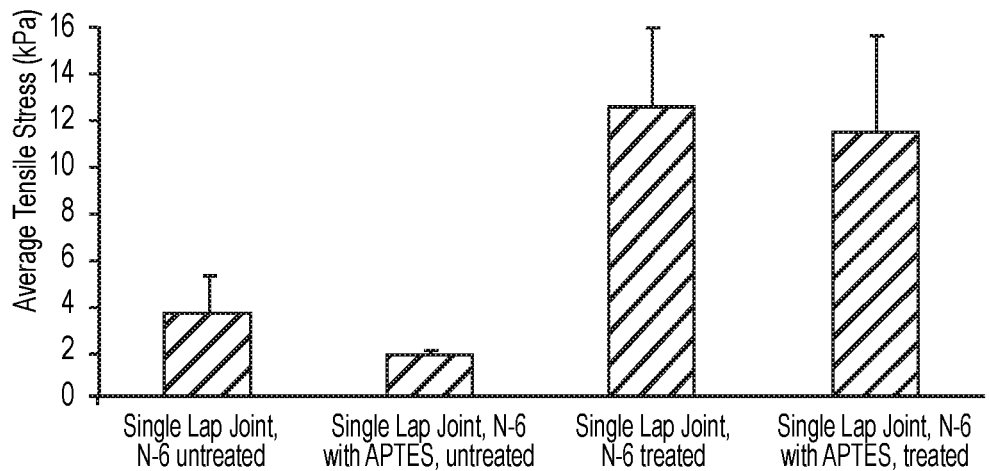

The adhesion tests were utilized to compare adhesive forces between Nylon-6 samples with and without the (3-aminopropyl) triethoxysilane (APTES) silane additive and with and without a heat treatment (150° C. for 1 hour; used in the PEDOT lithography development process). These results are presented in FIGS. 22A-22B. No significant differences were observed in the results of the T-peel testing. This result suggests that the investigated addition of APTES with the heat treatment failed to have a significant effect on normal adhesion forces of Nylon-6 nanofiber self-adhesion. Interestingly, it appears that the post-production heat treatment did have a significant ($p<0.05$) effect on the adhesive strength exhibited by these samples. It is hypothesized that heating the samples above the glass transition temperature of Nylon-6 (47° C.) caused Nylon-6 chain entanglement at the interface between the fibers of each layer; when normalized across the bound lap area, the magnitude of this increased adhesion is highly apparent. This test further suggests that the APTES is not currently contributing to the adhesion forces possessed by these samples. However, the addition of the heat-treatment protocol step appears to notably increase the shear stress required to separate the two layers, which is a valuable property for an in vivo construct. The formulation of a "single layer" system in which the PEDOT and silicone are all infused within that Nylon-6 nanofiber layer will eliminate all concerns for delamination of the electrode upon implantation/prolonged hydration.

Cytocompatibility Characterization

Cytocompatibility screenings using the Nylon-6/PEDOT samples with and without Parylene-C and APTES additives have been completed. Samples were cultured in direct contact with S42 rat Schwann cells and the LDH and MTT assays were used to characterize resultant cytocompatibility. Overall, it was observed that the cells appeared to be healthy in appearance with typical morphology when cultured in contact with the Nylon-6 samples with Parylene-C, APTES, or VPP PEDOT. However, those cultures incubated with Nylon-6+PEDOT:PSS (with or without DMSO) were observed to contain adherent cells of low-to-moderate health that were notably less robust and possessed atypical morphology potentially indicative of toxic effects. Cell viability (MTT) assay results suggested that these cytocompatibility issues were due to an undefined leachant from the fabrication process. Assessment of samples with and without DMSO or mold release were tested, and the results of these experiments indicated that the leachant was likely from the PEDOT:PSS component. Though the effects were only moderate, the PEDOT:PSS appears to have been the main contributor of toxicity in these studies, potentially due to a contaminant, stock purity, or some aspect of preparation or handling. Luna found that the application of a negative charge (−0.5V) to the conductive samples in PBS resulted in an increase in cellular attachment of rat Schwann cells (S42; ATCC CRL-2942) to the samples. These results were confirmed with both the MTT Assay and LIVE/DEAD staining. In an effort to assess if these changes were due to the charge application or rinse step, the cytocompatibility of a variety of sample treatments, including PEDOT:PSS and VPP PEDOT with and without rinse and charge steps, was assessed.

Cytocompatibility of the samples was assessed in both direct and indirect culture formats. Controls consisted of low-density polyethylene (LDPE; negative toxicity), natural rubber latex (positive toxicity), and cell-only (baseline). In the direct format, 8 mm material samples were incubated directly with S42 cell cultures for 24 hours. Following incubation, cell viability was visually observed and the MTT assay was used to confirm. The indirect method comprised extraction of materials into solution, with the extraction solution then incubated with cultures. The protocol was based upon the recommendations from ISO 10993 Biological Evaluation of Medical Devices for in vitro cytotoxicity testing, with 8 mm dressings extracted in culture media (1.3 $cm^2$/mL) containing 10% Fetal Bovine Serum (FBS) at 37° C. and 5.0% $CO_2$ for approximately 24 hours.

Figure 23A:
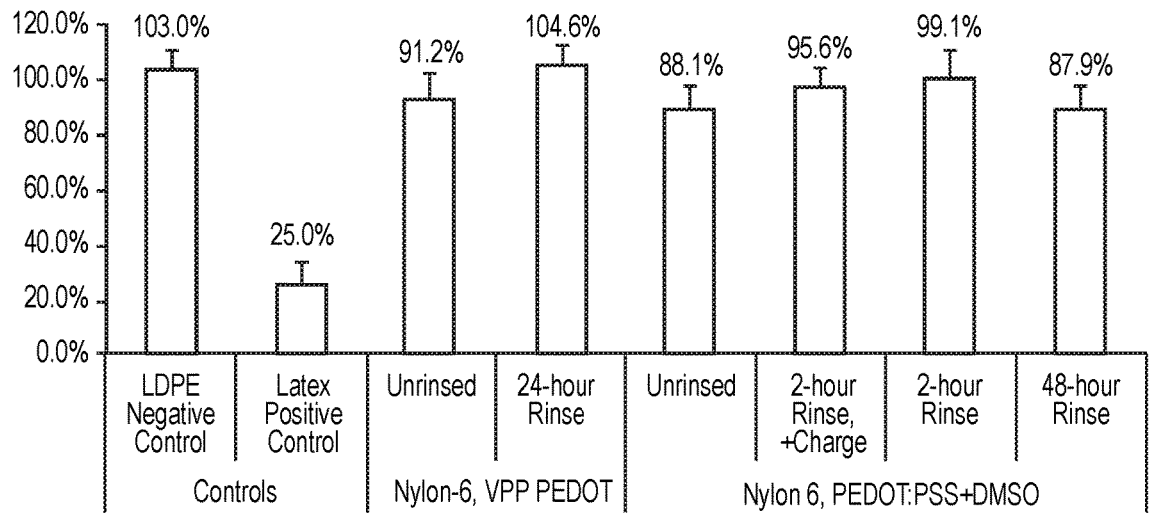
FIGS. 23A and 23B are bar graphs of direct and indirect cytotoxicity tests, respectively, showing cell viability following direct material exposure.

In the direct exposure study, cells incubated with rinsed dressing materials were observed to be generally healthy in appearance with typical morphology, qualitatively consistent with the cell-only baseline and LDPE negative toxicity controls. Only very mild phenotypic signs of toxicity apparent with the unrinsed Nylon-6 PEDOT:PSS/DMSO material within the direct format test was observed. The effects were significantly less pronounced than the strong response to the latex positive control, with nearly all cells rounded and detaching, a clear sign of poor health and low viability. Cultures exposed to rinsed variants of Nylon-6 VPP PEDOT and Nylon-6 PEDOT:PSS/DMSO showed no effects of toxicity, with no clear differences between culture sets. Finally, culture appearance was consistent for Nylon-6 PEDOT:PSS/DMSO material treated with a 2-hour rinse with and without a −0.5 V charge, indicating that charge was likely a neutral variable. These results were confirmed with the MTT assay results, shown in FIG. 23A. High viability was observed for both of the Nylon-6/VPP PEDOT variants, and showed increasing viability for the PEDOT:PSS/DMSO test samples with increasing rinses. For the Nylon-6 PEDOT:PSS/DMSO, there were no statistical differences between the 2-hour rinse with and without a −0.5 V charge, indicating the charge was likely a neutral variable. By ANOVA and Tukey analysis, only the unrinsed and 48-hour rinsed Nylon-6 PEDOT:PSS/DMSO were statistically less viable than the LDPE negative control ($p=0.01$), and suggestively less viable for the unrinsed Nylon-6 VPP PEDOT ($p=0.08$). This supported the qualitative observations and indicated that toxic components present in each chemistry were sufficiently reduced by the inclusion of a rinse process.

Figure 23B:
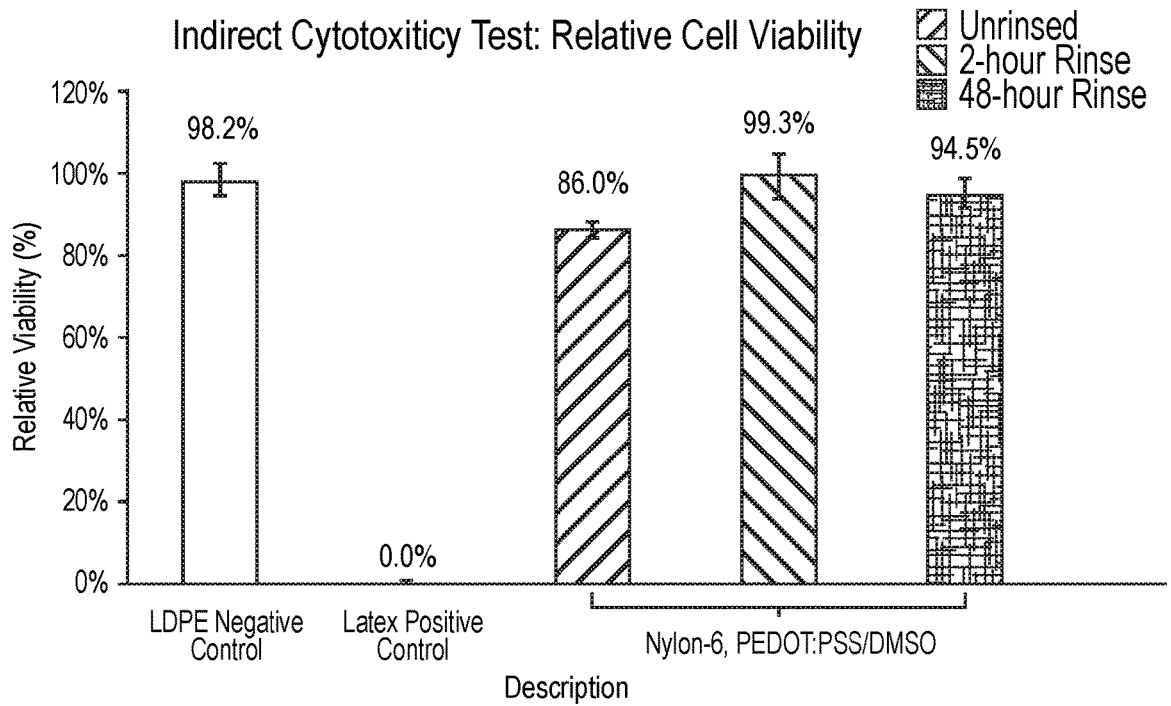

For the indirect study, there were again only slight visible signs of toxicity in cultures with extract from the unrinsed Nylon-6 PEDOT:PSS/DMSO. The mild effects here were more easily observed as rounded, adherent cells; this was significantly less pronounced than the latex positive toxicity control extract, in which nearly all cells were rounded and detached. Cells cultured with the 2-hour and 48-hour rinsed Nylon-6 PEDOT:PSS/DMSO extract material appeared comparably healthy and similar to negative control cultures, which indicated that both rinse protocols sufficiently reduced the presence of toxic components in dressings. Again, these results were confirmed with the MTT assay (FIG. 23B). By ANOVA and Tukey post-hoc analysis, only the cell viability for the unrinsed sample extract was statistically lower than the LDPE negative control ($p<0.001$), with both rinsed samples statistically comparable. This supported the qualitative observations and indicated that the toxic components present in the Nylon-6 PEDOT:PSS/DMSO chemistry were sufficiently reduced by a rinse process. All test and negative controls were less than the latex positive control ($p \leq 1 \times 10^{-8}$). There were no statistically significant differences between the 2 and 48-hour rinse treatments, which showed no clear benefit for a short vs. prolonged rinse process for toxicant extraction.

Collectively, these findings generally suggest cytocompatibility and confirm the benefit of post-preparation immersion rinsing in DPBS. Observations and assay results here indicated that mild cytotoxicity with unrinsed Nylon-6 PEDOT:PSS/DMSO and Nylon-6 VPP PEDOT was effectively reduced in both chemistries by the inclusion of a post-preparation DPBS rinse. This rinse step successfully allowed for toxic residuals to be leached from the material, thereby reducing the cytotoxicity for the rinsed dressings. Thus, both the rinsed VPP PEDOT and PEDOT:PSS-based materials have been determined to be suitable, cytocompatible candidates for the conductive attribute in the final dressings.

Sterility Characterization

Sterilization and cytocompatibility of the materials and systems were investigated. Sterilization was performed using both gamma irradiation (Steris Isomedix) and ethylene oxide treatment. Sterility was confirmed using the direct inoculation (immersion) technique in Fluid Thioglycolate and Trypticase Soy Broths, with no detrimental effects on electrical, mechanical, or biological properties.

In Vivo Characterization

The neuro devices have been investigated in an in vivo model for hindlimb electrode implantation for neural interfacing. To prepare for implantation, the rat sciatic nerve was exposed near its trifurcation; the TIME electrode implant is intended for placement into the tibial branch. An 80 μm diameter tungsten needle with a trailing loop of Kevlar fiber was used to pierce the nerve fascicle, and the loop was drawn through. After the needle was drawn through, the loop was pulled to a position where it intersected the introducer tip of the TIME interface to be implanted. This loop was pulled closed over the electrode's introducer tip, and pulled the electrode into the nerve.

To increase electrode stability during implantation, the TIME interface was attached to a cuff electrode placed over the upper portion of the nerve. In order to prevent the introducer loop slipping off of the electrode tip during implantation, a Kevlar "support fiber" was attached. The nanofiber-based electrode freely conformed during implantation with no critical bend radius observed. In fact, such flexibility has been identified as a cause for possible introducer tip slipping out of the Kevlar introducer loop during implantation.

Figure 24:
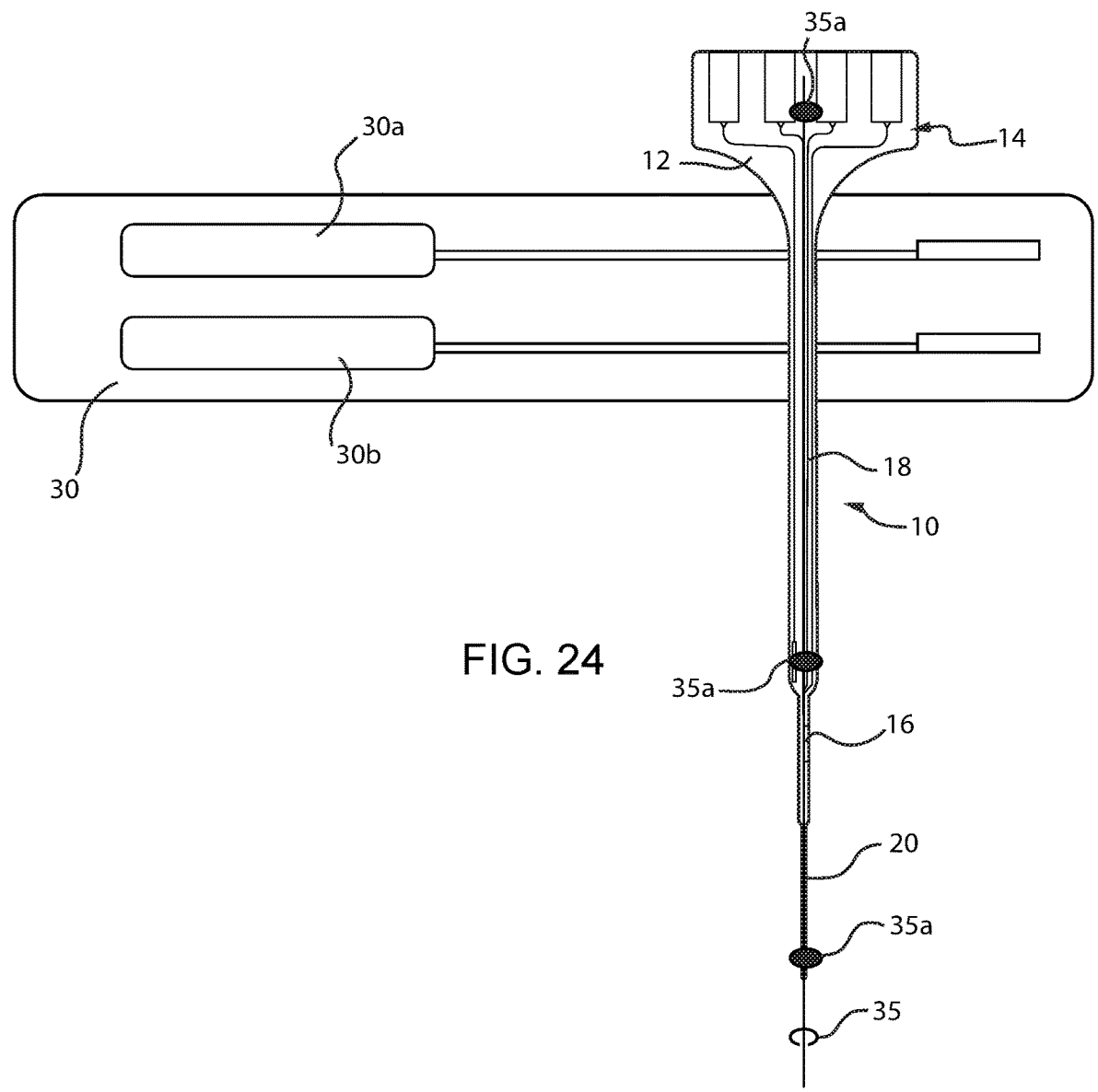
FIG. 24 is a schematic depiction of a TIME interface prepared for implantation which includes a neural interface device in accordance with an embodiment of this invention.

As noted briefly above, a method has also been developed to attach the TIME interface 14 to a cuff electrode 30 having electrode contacts 30a, 30b for stabilization during the implant process. Such an embodiment is depicted in FIG. 24.

In addition to attaching the TIME interface 14 to the cuff electrode 30 for stabilization, a Kevlar fiber 35 is adhered over the length of the electrode 10 to reduce tensile stress on the electrode 10. The dots 35*a* indicate areas of potential attachment of the Kevlar fiber 35 to the TIME interface 14. The process of anchoring the electrode is simplified by the addition of the Kevlar support fiber 35 onto the TIME interface 14. After successful electrode implantation, the Kevlar fiber 35 over the intrafascicular portion can be cut and pulled out of the nerve. The separate ends of this fiber 35 will now be on either side of the nerve, and serve as attachment points where suture can be tied to hold the electrode in place. Advanced packaging systems have been designed to facilitate implantation and eliminate subsequent movement of the device that will impact recording. These systems have been demonstrated in vivo using Qualia control electrodes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

[1] The entire content of each of the References cited is expressly incorporated hereinto by reference.

REFERENCES[1]

1. Barrese, J. C. et al. Failure mode analysis of silicon-based intracortical microelectrode arrays in non-human primates. *J. Neural Eng.* 10, 66014 (2013).
2. Capadona, J. R., Tyler, D. J., Zorman, C. a., Rowan, S. J. & Weder, C. Mechanically adaptive nanocomposites for neural interfacing. *MRS Bull.* 37, 581-589 (2012).
3. Jeong, J.-W. et al. Soft Materials in Neuroengineering for Hard Problems in Neuroscience. *Neuron* 86, 175-186 (2015).
4. Kim, Y. & Romero-Ortega, M. I. Material considerations for peripheral nerve interfacing. *MRS Bull.* 37, 573-580 (2012).
5. Yoshida, K., Member, S., Stieglitz, T., Qiao, S. & Member, S. Bioelectric Interfaces for the Peripheral Nervous System. *36th Annu. Int. Conf. IEEE Eng. Med. Biol. Soc.* 5272-5275 (2014). doi:10.1109/EMBC.2014.6944815
6. Ware, T. et al. Fabrication of Responsive, *Softening* Neural Interfaces. *Adv. Funct. Mater.* 22, 3470-3479 (2012).
7. Andrei, a, Welkenhuysen, M., Nuttin, B. & Eberle, W. A response surface model predicting the in vivo insertion behavior of micromachined neural implants. *J. Neural Eng.* 9, 16005 (2011).
8. Bjornsson, C. S. et al. Effects of insertion conditions on tissue strain and vascular damage during neuroprosthetic device insertion. *J. Neural Eng.* 3, 196-207 (2006).
9. Boretius, T. et al. A transverse intrafascicular multichannel electrode (TIME) to interface with the peripheral nerve. *Biosens. Bioelectron.* 26, 62-69 (2010).
10. Navarro, X. et al. A Critical Review of Interfaces with the Peripheral Nervous System for the Control of Neuroprotheses and Hybrid Bionic Systems. *J Peripher Nerv Syst* 10, 229-258 (2005).
11. Di Pino, G. et al. Invasive neural interfaces: the perspective of the surgeon. *J. Surg. Res.* 188, 77-87 (2014).
12. Mandal, H. S. et al. Improving the performance of poly(3,4-ethylenedioxythiophene) for brain-machine interface applications. *Acta Biomater.* 10, 2446-2454 (2014).
13. Wang, Y. et al. A highly stretchable, transparent, and conductive polymer. 1-11 (2017).
14. Kumarathasan, P. et al. Cytotoxicity of carbon nanotube variants: A comparative in vitro exposure study with A549 epithelial and J774 macrophage cells. *Nanotoxicology* 9, 1743-5390 (2015).
15. Casey, A. et al. Probing the interaction of single walled carbon nanotubes within cell culture medium as a precursor to toxicity testing. *Carbon N. Y.* 45, 34-40 (2007).
16. Gladwin, K. M., Whitby, R. L. D., Mikhalovsky, S. V., Tomlins, P. & Adu, J. In Vitro Biocompatibility of Multiwalled Carbon Nanotubes with Sensory Neurons. *Adv. Healthc. Mater.* 2, 728-735 (2013).

What is claimed is:

1. A method of making a flexible electrode comprising the steps of:
    (a) electrospinning a nanofiber mat comprised of a nonwoven mass of polymeric nanofibers;
    (b) depositing a conductive component on or within the nanofiber mat; and
    (c) photolithographically forming electrical traces on or within the nanofiber mat.

2. The method according to claim 1, which further comprises the step of:
    (d) coating the nanofiber mat and electrical traces with a silicone layer; and thereafter
    (e) etching regions of the silicone layer to form contact points.

3. The method according to claim 2, which further comprises the step of:
    (f) forming a final shape of the electrode.

4. The method according to claim 1, wherein step (b) comprises applying a photoresist material onto the nanofiber mat and etching conductive channel patterns.

5. The method according to claim 4, wherein step (b) comprises incorporating an electrically conductive material in the channel patterns.

6. The method according to claim 1, wherein between steps (a) and (b) there is practiced a step of:
    (a1) depositing a photoresist onto the nanofiber mat and allowing the photoresist to fill a lower region of the nanofiber mat and thereby coat the polymeric nanofibers therein and establish a top surface region of the nanofiber mat comprised of polymeric nanofibers uncoated by the photoresist.

7. The method according to claim 6, wherein step (b) comprises:
    (b1) depositing a conductive metal layer onto the top surface region of the nanofiber mat to provide a layer of conductive metal-coated polymeric nanofibers in at least a portion of the top surface region thereof.

8. The method according to claim 7, wherein step (c) comprises:
    (c1) photolithographically forming electrical traces of the conductive metal-coated polymeric nanofibers in the top surface region of the nanofiber mat.

9. The method according to claim 8, which further comprises the steps of:
    (d) applying silicone onto the nanofiber mat to form a silicone layer over the electrical traces; and thereafter
    (e) etching regions of the silicone layer to form contact points of the electrical traces.

10. The method according to claim 9, which further comprises the step of:
    (f) forming a final shape of the electrode.

11. The method according to claim 8, which further comprises the step of:
   (d) applying silicone onto the nanofiber mat to form a silicon-filled nanofiber mat and a silicone layer over the electrical traces.

12. The method according to claim 11, wherein the silicone layer has a thickness of about 5 μm.

13. The method according to claim 11, which further comprises the step of:
   (f) etching regions of the silicone layer to form contact points of the electrical traces.

14. The method according to claim 6, wherein step (a) comprises providing a silicon wafer, and electrospinning the nanofiber mat onto the silicon wafer.

15. The method according to claim 1, wherein the nanofiber mat fibrous substrate exhibits an elastic modulus of between about 50 MPa to about 5 GPa.

16. The method according to claim 15, wherein the polymeric nanofibers comprise an insulating coating.

17. The method according to claim 15, wherein the nanofiber mat substrate comprises a nanofiber layer which includes the polymeric nanofibers and an insulation layer.

18. The method according to claim 17, wherein the insulation layer comprises a p-xylyene polymer or polydimethysiloxane.

19. The method according to claim 1, wherein the polymeric nanofibers are formed of a plastic material selected from the group consisting of nylon, polycaprolactone, cellulose acetate, poly(methyl-methacrylate, ethylene vinyl alcohol and polyimide.

20. The method according to claim 1, wherein the polymeric nanofibers are formed of nylon-6 and/or nylon-6,12.

* * * * *